United States Patent
Schoop et al.

(10) Patent No.: US 6,291,503 B1
(45) Date of Patent: *Sep. 18, 2001

(54) β-PHENYLALANINE DERIVATIVES AS INTEGRIN ANTAGONISTS

(75) Inventors: Andreas Schoop, Overath; Gerhard Mueller, Leverkusen, both of (DE); Ulf Brueggemeier, Madison, CT (US); Delf Schmidt, Wuppertal (DE); Beatrix Stelte-Ludwig, Wuelfrath (DE); Joerg Keldenich, Wuppertal (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/232,738

(22) Filed: Jan. 15, 1999

(51) Int. Cl.$^7$ .................. A01N 43/56; A01N 37/12; C07D 233/66; C07C 317/14; C07C 315/04

(52) U.S. Cl. ............... 514/401; 514/539; 514/562; 548/333.1; 560/13; 560/34; 562/430; 562/439

(58) Field of Search ............... 560/13, 34; 562/430, 562/439, 4; 548/333.1; 514/401, 539, 562

(56) References Cited

U.S. PATENT DOCUMENTS 5,639,765 * 6/1997 Ruminski ............... 514/329

FOREIGN PATENT DOCUMENTS

| | | |
|---|---|---|
| WO 97/08145 | 3/1997 | (WO) . |
| WO 97/36858 | 10/1997 | (WO) . |
| WO 97/36859 | 10/1997 | (WO) . |
| WO 97/36860 | 10/1997 | (WO) . |
| WO 97/36861 | 10/1997 | (WO) . |
| WO 97/36862 | 10/1997 | (WO) . |
| WO 98/00395 * | 1/1998 | (WO) ............ C07C/311/06 |
| WO 98/18461 | 5/1998 | (WO) . |
| WO 99/23063 | 5/1999 | (WO) . |

OTHER PUBLICATIONS

Database CAPLUS on STN, Acc. No. 1993:7363, Alig et al., 'Low molecular weight, non–peptide fibrinogen receptor antagonists,' J. Med. Chem. (1992), 35(23), pp. 4393–4407 (abstract), 1992.*

Cardiovascular Research 1994; 28: 1815–1820; Steven L. Brown, et al., 'Stimulation of migration of human aortic smooth muscle cells by vitronectin: implications for atherosclerosis", p. 2, last line.

Aromatic Aldehyde–Malonic Acid Condensations, Mar. 1929; vol. 51; pp. 841–847; W. M. Rodionow, et al.; "The Mechanism of Formation of Beta–Aryl–Beta–Amino Fatty Acids by the Condensation of Aromatic Aldehydes with Malonic Acid and its Derivatives", p. 45, lines 20–21.

Angew.Chem. 101 (1989) Nr. 8; pp. 1042–1043; Von Horst Kunz, et al.; "Kohlenhydrate als chirale Matrices: Stereoselektive Synthese von β–Aminosäuren", p. 45, line 21.

Bull Chem. Soc. Jpn., 68, 1721–1730 (1995); Kazuaki Ishihara, et al.; "Tris(pentafluorophenyl) boron as an Efficient, Air Stable, and Water Tolerant Lewis Acid Catalyst", p. 48, lines 21–22.

Cell, Vol. 79, 1157–1164 Dec. 30, 1994, Cell Press; Peter C. Brooks, et al.; "Integrin αvβ3 Antagonists Promote Tumor Regression by Inducting Apoptosis of Angiogenic Blood Vessels", p. 2, lines 17–18.

J. Clin. Invest; The American Society for Clinical Investigation, Inc., vol. 96, Oct. 1995, 1815–1822; Peter C. Brooks, et al.; "Antiintegrin αvβ3 blocks human breast cancer growth and angiogenesis in human skin", p. 2, line 22.

* cited by examiner

Primary Examiner—Johann Richter
Assistant Examiner—Brian J. Davis
(74) Attorney, Agent, or Firm—Norris, McLaughlin & Marcus, P.A.

(57) ABSTRACT

The present invention relates to compounds of the general formula (1)

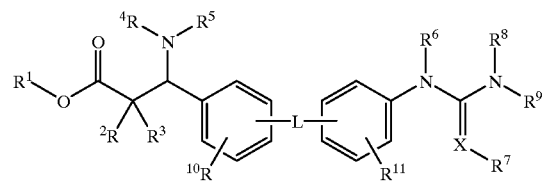

(1)

wherein $R^4$ is $-SO_2R^{4'}$, $-COOR^{4'}$, $-COR^{4'}$, $-CONR^{4'}_2$ or $-CSNR^{4'}_2$; $R^{4'}$ is hydrogen, a substituted or unsubstituted alkyl or cycloalkyl residue, a substituted or unsubstituted aryl residue or a saturated or unsaturated, optionally substituted heterocyclic residue; $R^{4''}$ is a substituted or unsubstituted alkyl or cycloalkyl residue, a substituted or unsubstituted aryl residue or a saturated or unsaturated, optionally substituted heterocyclic residue; L is a sulphonamide, amide, ether, ester, keto, urea, thioether, sulphoxide or sulphone unit optionally extended by one or two methylene groups; and X is N, O or S; and their physiologically acceptable salts and stereoisomers. The present invention furthermore relates to a process for the preparation of the compounds of the formula (1), a pharmaceutical composition containing at least one of these compounds, and the use of compounds of the formula (1) for the production of a pharmaceutical composition having integrin-antagonistic action and in particular for the therapy and prophylaxis of cancer, osteolytic diseases such as osteoporosis, arteriosclerosis, restenosis and ophthalmic disorders.

14 Claims, No Drawings

β-PHENYLALANINE DERIVATIVES AS INTEGRIN ANTAGONISTS

FIELD OF THE INVENTION

The present invention relates to β-phenylalanine derivatives, their preparation and use as pharmaceutical compositions, as integrin antagonists and in particular for the production of pharmaceutical compositions for the treatment and prophylaxis of cancer, arteriosclerosis, restenosis, osteolytic disorders such as osteoporosis and ophthalmic diseases.

BACKGROUND OF THE INVENTION

Integrins are heterodimeric transmembrane proteins located on the surface of cells, which play an important part in the adhesion of cells to an extracellular matrix. They recognize extracellular glycoproteins such as fibronectin or vitronectin on the extracellular matrix by means of the RGD sequence occurring in these proteins (RGD is the single-letter code for the amino acid sequence arginine-glycine-aspartate).

In general, integrins such as, for example, the vitronectin receptor, which is also referred to as the $\alpha_v\beta_3$ receptor, or alternatively the $\alpha_v\beta_,$ receptor or the GpIIb/IIIa receptor, play an important part in biological processes such as cell migration and cell-matrix adhesion and thus in diseases in which these processes are crucial steps. Examples which may be mentioned are cancer, osteoporosis, arteriosclerosis, restenosis (fresh occurrence of a stenosis after a surgical intervention as a result of damage to the vascular wall) and ophthalmia (a certain type of inflammation of the eye).

The $\alpha_v\beta_3$ receptor occurs, for example, in large amounts on growing endothelial cells and makes possible their adhesion to an extracellular matrix. Thus the $\alpha_v\beta_3$ receptor plays an important part in angiogenesis, i.e. the formation of new blood vessels, which is a crucial requirement for tumor growth and metastasis formation in carcinomatous disorders. Furthermore, it is also responsible for the interaction between osteoclasts, i.e. cells resorbing mineralized tissue, and the bone structure. The first step in the degradation of bone tissue consists in adhesion of osteoclasts to the bone. This cell-matrix interaction takes place via the $\alpha_v\beta_3$ receptor, which is why the corresponding integrin plays an important part in this process. Osteolytic diseases such as osteoporosis are caused by an inequilibrium between bone formation and bone degradation, i.e. the resorption of bone material caused by addition of osteoclasts predominates.

It was possible to show that the blocking of the above-mentioned receptors is an important starting point for the treatment of disorders of this type. If the adhesion of growing endothelial cells to an extracellular matrix is suppressed by blocking their corresponding integrin receptors, for example by a cyclic peptide or a monoclonal antibody, the endothelial cells die. Angiogenesis therefore does not occur, which leads to a stoppage or regression of tumour growth (cf., for example, Brooks et al., Cell, Volume 79, 1157–1164, 1994).

Moreover, the invasive properties of tumour cells and thus their ability for metastasis formation are markedly decreased if their $\alpha_v\beta_3$ receptor is blocked by an antibody (Brooks et al., J. Clin. Invest., Volume 96, 1815, 1995).

The degradation of bone tissue can obviously be suppressed by blockage of the $\alpha_v\beta_3$ receptors of the osteoclasts, since these are then unable to accumulate on the bone in order to resorb its substance (WO 98/18461, p. 1, 1.24 to p.2,1. 13).

As a result of the blockage of the $\alpha_v\beta_3$ receptor on cells of the aorta smooth vascular musculature with the aid of integrin receptor antagonists, it is possible to suppress the migration of these cells into the neointima and thus angioplasty leading to arteriosclerosis and restenosis (Brown et al., Cardiovascular Res., Volume 28, 1815, 1994).

In recent years, compounds have therefore been sought which act as antagonists of integrin receptors. For example, WO98/00395 discloses the para-substituted phenylalanine derivative (I), which exhibits an $IC_{50}$ value of 0.13 nM in an $\alpha_v\beta_3$ receptor assay and an $IC_{50}$ value of 0.16 nM in an $\alpha_v\beta_5$ receptor assay:

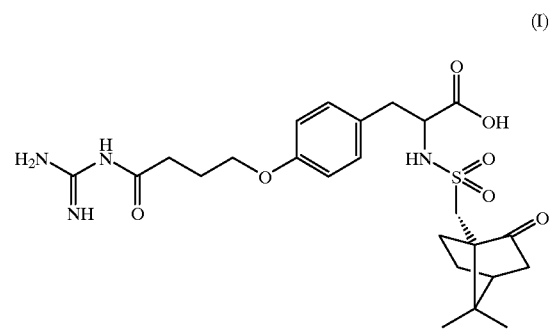

(I)

ω-Phenylcarboxylic acids having a phenyl residue which is linked to the phenyl group via a linker group and having a guanidine unit or a guanidine mimic are disclosed, for example in WO 97/36858, WO 97/36859, WO 97/36860 and WO 97/36862. According to these laid-open patent applications, the linker group can be an amide, sulphonamide, ester, urea, ether, thioether, sulphoxide, sulphone or ketone unit which may be extended by an additional methylene group, or can be a saturated or unsaturated alkylene bridge.

In particular, WO 97/36859, in addition to numerous substances comprised by a general formula, actually discloses 3-phenylpropionic acid derivatives such as (II) or (III). While the α-phenylalanine derivative (II) exhibits an $IC_{50}$ value of 0.18 nM with respect to its activity as an $\alpha_v\beta_3$ antagonist in in-vitro investigations, the succinic acid derivatives (III) have $IC_{50}$ values in the range from 38.7 to 141 nM in the same investigations:

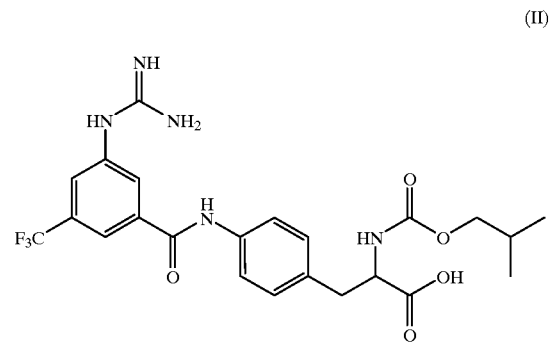

(II)

-continued

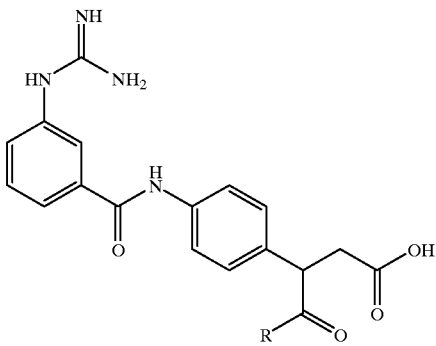

(III)

R=OH, OEt, NHCH$_2$COOH

WO 97/36862, in addition to numerous substances comprised by a general formula, actually describes β-substituted propionic acid derivatives such as (IV) or (V). The sulphonamide-bridged derivative (IV) exhibits an IC$_{50}$ value of 16.7 nM with respect to its activity as an α$_v$β$_3$ antagonist in in-vitro investigations, while the amide-bridged derivatives (V) have IC$_{50}$ values in the range from 0.87 to 11.6 nM in the same investigations:

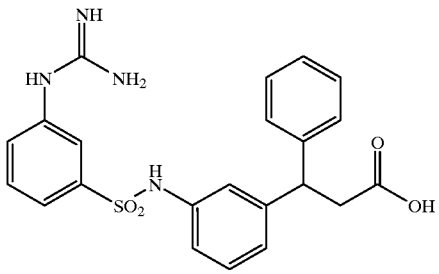

(IV)

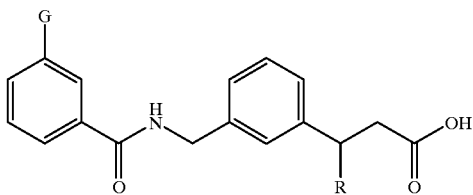

(V)

R=methyl, isopropyl, phenyl, 3,5-difluorophenyl

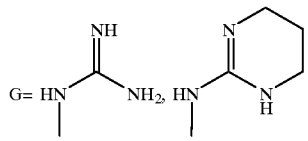

None of the abovementioned laid-open patent applications, however, discloses β-phenylalanine derivatives or their activity as α$_v$β$_3$ antagonists.

β-Phenylalanine derivatives as α$_v$β$_3$ antagonists are disclosed, for example, in U.S. Pat. No. 5,639,765, WO 97/08145 and WO 97/36861, the linkage of the carboxyl residue to the central group consisting of two phenyl units bonded to one another via a linker group being carried out in these compounds, if a central group of this type is present at all, via the amino group. For example, the compound (VI) disclosed in WO 97/36861 exhibits an IC$_{50}$ value of 1.66 nM with respect to its activity as an α$_v$β$_3$ antagonist in in-vitro investigations.

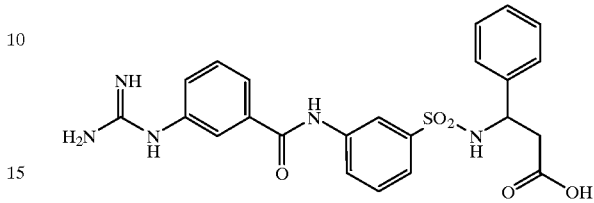

(VI)

It was the object of the present invention to develop compounds which exhibit a high activity as integrin antagonists and in particular against the α$_v$β$_3$ and/or the α$_v$β$_3$ receptor.

SUMMARY OF THE INVENTION

The present object is achieved according to the invention by the β-phenylalanine derivatives defined below. In particular, it has emerged that the β-phenylalanine derivatives according to the invention have a very high activity as integrin antagonists, especially against the α$_v$β$_3$ and/or the α$_v$β$_5$ receptor.

The present invention relates to compounds of the general formula (1)

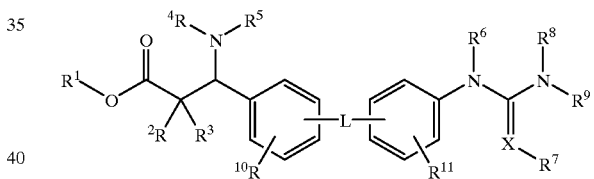

(1)

wherein

R$^1$ is hydrogen, a substituted or unsubstituted alkyl or cycloalkyl residue, a substituted or unsubstituted aryl residue or a saturated or unsaturated, optionally substituted heterocyclic residue;

R$^2$ is hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, a hydroxyl residue or an alkoxy residue or is bonded to R$^3$ with formation of an optionally substituted carbocyclic or heterocyclic ring system which includes the carbon atom to which R$^2$ is bonded and can optionally contain heteroatoms;

R$^3$ is hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, a hydroxyl residue or an alkoxy residue or is bonded to R$^2$ with formation of an optionally substituted carbocyclic or heterocyclic ring system which includes the carbon atom to which R$^3$ is bonded and can optionally contain heteroatoms;

$R^4$ is —$SO_2R^{4'}$, —$COOR^{4''}$, —$COR^{4'}$, —$CONR^{4'}_2$ or —$CSNR^{4'}_2$;

$R^{4'}$ is hydrogen, a substituted or unsubstituted alkyl or cycloalkyl residue, a substituted or unsubstituted aryl residue or a saturated or unsaturated, optionally substituted heterocyclic residue;

$R^{4''}$ is a substituted or unsubstituted alkyl or cycloalkyl residue, a substituted or unsubstituted aryl residue or a saturated or unsaturated, optionally substituted heterocyclic residue;

$R^5$ is hydrogen, a substituted or unsubstituted alkyl or cycloalkyl residue or a substituted or unsubstituted aryl residue;

$R^{10}$ is hydrogen, a substituted or unsubstituted alkyl or cycloalkyl residue, a substituted or unsubstituted alkoxy residue or a halogen atom;

$R^{11}$ is hydrogen, a substituted or unsubstituted alkyl or cycloalkyl residue, a substituted or unsubstituted alkoxy residue or a halogen atom;

L is —$(CH_2)_m NHSO_2(CH_2)_n$—, —$(CH_2)_m SO_2NH(CH_2)_n$—, —$(CH_2)_m NHCO(CH_2)_n$—, —$(CH_2)_m CONH(CH_2)_n$—, —$(CH_2)_m OCH_2(CH_2)_n$—, —$(CH_2)_m CH_2O(CH_2)_n$—, —$(CH_2)_m COO(CH_2)_n$—, —$(CH_2)_m OOC(CH_2)_n$—, —$(CH_2)_m CH_2CO(CH_2)_n$—, —$(CH_2)_m COCH_2(CH_2)_n$—, —$NHCONH$—, —$(CH_2)_m SCH_2(CH_2)_n$—, —$(CH_2)_m CH_2S(CH_2)_n$—, —$(CH_2)_m CH_2SO(CH_2)_n$—, —$(CH_2)_m SOCH_2(CH_2)_n$—, —$(CH_2)_m CH_2SO_2(CH_2)_n$— or —$(CH_2)_m SO_2CH_2(CH_2)_n$—, wherein m and n are each an integer of 0 or 1 and m+n≦1;

$R^6$ is hydrogen, a substituted or unsubstituted alkyl or cycloalkyl residue, a substituted or unsubstituted aryl residue, a saturated or unsaturated, optionally substituted heterocyclic residue or is bonded to one of $R^7$, $R^8$ or $R^9$, if present, with formation of an optionally substituted heterocyclic ring system which includes the nitrogen atom to which $R^6$ is bonded and can be saturated or unsaturated and/or can contain further heteroatoms;

X is N, O or S;

$R^7$ is absent, is —H, a substituted or unsubstituted alkyl or cycloalkyl residue, —$NO_2$, —CN, —$COR^{7'}$, —$COOR^{7'}$, or is bonded to one of $R^6$, $R^8$ or $R^9$ with formation of an optionally substituted heterocyclic ring system which includes X and can be saturated or unsaturated and/or can contain further heteroatoms;

$R^{7'}$ is hydrogen, a substituted or unsubstituted alkyl or cycloalkyl residue, a substituted or unsubstituted aryl residue or a saturated or unsaturated, optionally substituted heterocyclic residue which can be saturated or unsaturated and/or can contain further heteroatoms;

$R^8$ is hydrogen, a substituted or unsubstituted alkyl or cycloalkyl residue, a substituted or unsubstituted aryl residue, a saturated or unsaturated, optionally substituted heterocyclic residue or is bonded to one of $R^6$, $R^7$ or $R^9$, if present, with formation of an optionally substituted heterocyclic ring system which includes the nitrogen atom to which $R^8$, is bonded and can be saturated or unsaturated and/or can contain further heteroatoms;

$R^9$ is hydrogen, a substituted or unsubstituted alkyl or cycloalkyl residue, a substituted or unsubstituted aryl residue, a saturated or unsaturated, optionally substituted heterocyclic residue or is bonded to one of $R^6$, $R^7$ or $R^8$, if present, with formation of an optionally substituted heterocyclic ring system which includes the nitrogen atom to which $R^9$ is bonded and can be saturated or unsaturated and/or can contain further heteroatoms;

and their physiologically acceptable salts and stereoisomers.

According to the invention, preferred compounds of the formula (1) are those in which $R^1$ is hydrogen, a $C_{1-6}$-alkyl residue, a $C_{3-7}$-cycloalkyl residue, an aryl residue or a substituted derivative thereof;

$R^2$ is hydrogen, a $C_{1-4}$-alkyl residue, a $C_{3-7}$-cycloalkyl residue, an aryl residue, an alkenyl residue, an alkinyl residue or a substituted derivative thereof; a hydroxyl residue or a $C_{1-4}$-alkoxy residue or is bonded to $R^3$ with formation of an optionally substituted carbocyclic or heterocyclic ring system which includes the carbon atom to which $R^2$ is bonded and can optionally contain heteroatoms;

$R^3$ is hydrogen, a $C_{1-6}$-alkyl residue, a $C_{3-7}$-cycloalkyl residue, an aryl residue, an alkenyl residue, an alkinyl residue or a substituted derivative thereof; a hydroxyl residue or a $C_{1-6}$-alkoxy residue or is bonded to $R^2$ with formation of an optionally substituted carbocyclic or heterocyclic ring system which includes the carbon atom to which $R^3$ is bonded and can optionally contain heteroatoms;

$R^4$ is —$SO_2R^{4'}$, —$COOR^{4''}$, —$COR^{4'}$, —$CONR^{4'}_2$ or —$CSNR^{4'}_2$;

$R^{4'}$ is hydrogen, a $C_{1-6}$-alkyl residue, a $C_{3-7}$-cycloalkyl residue, a substituted or unsubstituted aryl residue or a saturated or unsaturated, optionally substituted heterocyclic residue;

$R^{4''}$ is a $C_{1-6}$-alkyl residue, a $C_{3-7}$-cycloalkyl residue, a substituted or unsubstituted aryl residue or a saturated or unsaturated, optionally substituted heterocyclic residue;

$R^5$ is hydrogen, a $C_{3-6}$-alkyl residue, a $C_{3-7}$-cycloalkyl residue, a $C_{1-6}$-alkoxy residue or a substituted derivative thereof;

$R^{10}$ is hydrogen, a $C_{1-6}$-alkyl residue, a $C_{3-7}$-cycloalkyl residue, a $C_{1-6}$-alkoxy residue or a substituted derivative thereof or F, Cl, Br or I;

$R^{11}$ is hydrogen, a $C_{1-6}$-alkyl residue, a $C_{3-7}$-cycloalkyl residue, an aryl residue or a substituted derivative thereof or F, Cl, Br or I;

L is —$NHSO_2$—, —$CH_2NHSO_2$—, —$NHSO_2CH_2$—, —$SO_2NH$—, —$CH_2SO_2NH$—, —$SO_2NHCH_2$—, —$NHCO$—, —$CH_2NHCO$—, —$NHCOCH_2$—, —$CONH$—, —$CH_2CONH$—, —$CONHCH_2$—, —$OCH_2$—, —$CH_2OCH_2$, —$OCH_2CH_2$—, —$CH_2O$— —$CH_2CH_2O$—, —$COO$—, —$CH_2COO$—, —$COOCH_2$—, —$OOC$—, —$OOCCH_2$—, —$CH_2OOC$—, —$CH_2CO$—, —$COCH_2$—, —$CH_2CH_2CO$—, —$COCH_2CH_2$—, —$CH_2COCH_2$—, —$NHCONH$—, —$SCH_2$—, —$CH_2S$—, —$CH_2SCH_2$, —$SCH_2CH_2$—, —$CH_2CH_2S$—, —$SOCH_2$—, —$CH_2SO$—, —$CH_2SOCH_2$—, —$SOCH_2CH_2$—, —$CH_2CH_2SO$—, —$SO_2CH_2$—, —$CH_2SO_2$—, —$CH_2SO_2CH_2$—, —$CH_2CH_2SO_2$— or —$SO_2CH_2CH_2$—;

$R^6$ is hydrogen, a $C_{1-6}$-alkyl residue, a $C_{3-7}$-cycloalkyl residue, an aryl residue or a substituted derivative thereof or is bonded to one of $R^7$, $R^8$ or $R^9$, if present, with formation of an optionally substituted heterocyclic ring system which includes the nitrogen atom to which $R^6$ is bonded and can be saturated or unsaturated and/or can contain further heteroatoms;

X is O, N or S;

$R^7$ is absent, is —H, a $C_{1-6}$-alkyl residue, a $C_{3-7}$-cycloalkyl residue, —$NO_2$, —CN, —$COR^7$, —$COOR^7$, or is bonded to one of $R^6$, $R^8$ or $R^9$ with formation of an optionally substituted heterocyclic ring system which includes X and can be saturated or unsaturated and/or can contain further heteroatoms;

$R^{7'}$ is hydrogen, a $C_{1-6}$-alkyl residue, a $C_{3-7}$-cycloalkyl residue, an aryl residue or a substituted derivative thereof, R$^8$ is hydrogen, a C$_{1-6}$-alkyl residue, a C$_{3-7}$-cycloalkyl residue, an aryl residue or a substituted derivative thereof or is bonded to one of R$^6$, R$^7$ or R$^9$, if present, with formation of an optionally substituted heterocyclic ring system which includes the nitrogen atom to which R$^8$ is bonded and can be saturated or unsaturated and/or can contain further heteroatoms; and R$^9$ is hydrogen, a C$_{1-6}$-alkyl residue, a C$_{3-7}$-cycloalkyl residue, an aryl residue or a substituted derivative thereof or is bonded to one of R$^6$, R$^7$ or R$^8$, if present, with formation of an optionally substituted heterocyclic ring system which includes the nitrogen atom to which R$^9$ is bonded and can be saturated or unsaturated and/or can contain further heteroatoms.

Particularly preferred compounds of the formula (I) according to the present invention are those in which R$^1$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof;

R$^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —OH, methoxy, ethoxy, propoxy, butoxy, pentoxy, hexoxy, benzyloxy or is bonded to R$^3$ with formation of an optionally substituted 3- to 6-membered carbocyclic or heterocyclic ring system which includes the carbon atom to which R$^2$ is bonded and can optionally contain heteroatoms;

R$^3$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —OH, methoxy, ethoxy, propoxy, butoxy, pentoxy, hexoxy, or is bonded to R$^2$ with formation of an optionally substituted 3- to 6-membered carbocyclic or heterocyclic ring system which includes the carbon atom to which R$^3$ is bonded and can optionally contain heteroatoms;

R$^4$ is —SO$_2$R$^{4'}$ or —COR$^{4'}$;

R$^{4'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, Iphenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonylpiperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl, 8-quinolinyl;

R$^5$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, C$_{1-4}$-alkylamino-C$_{1-4}$-alkyl, C$_{1-4}$-dialkylamino-C$_{1-4}$-alkyl, amino-C$_{1-4}$-alkyl, C$_{1-4}$-alkyloxy-C$_{1-4}$-alkyl or

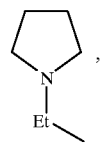

(a1)

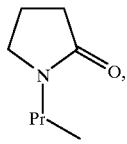

(a2)

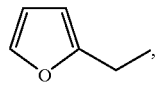

(a3)

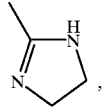

(a4)

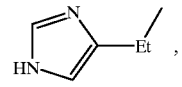

(a5)

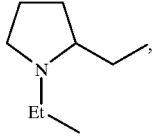

(a6)

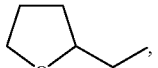

(a7)

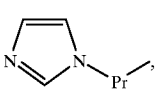

(a8)

-continued
(a9) 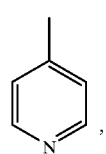
(a10) 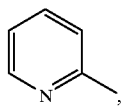
(a11) 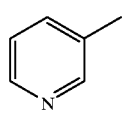
(a12) 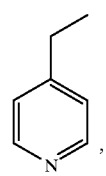
(a13) 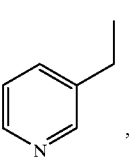
(a14) 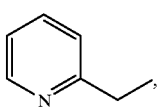
(a15) 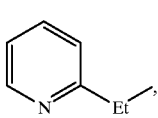
(a16) 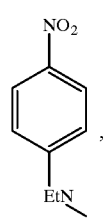
(a17) 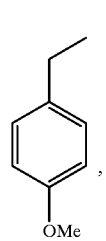
-continued
(a18) 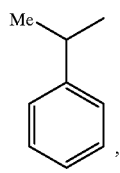
(a19) 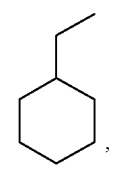
(a20) 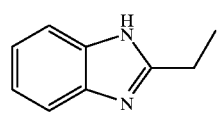
(a21) 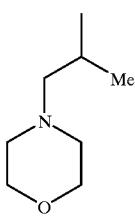
(a22) 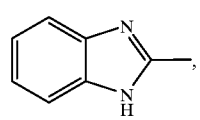
(a23) 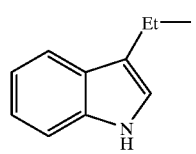
(a24) 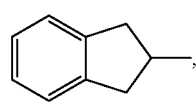
(a25) 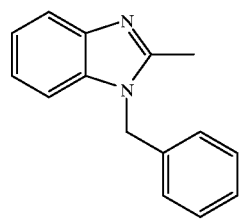
(a26) 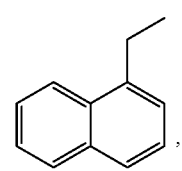

-continued

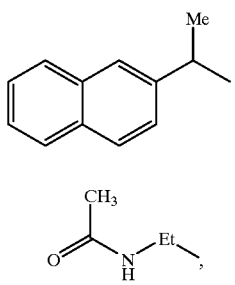
(a27)

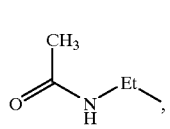
(a28)

R¹⁰ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, methoxy, ethoxy, propoxy, butoxy, pentoxy or hexoxy, fluorine, chlorine, bromine or iodine;

R¹¹ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, methoxy, ethoxy, propoxy, butoxy, pentoxy or hexoxy, fluorine, chlorine, bromine or iodine;

L is —NHSO₂—, —CH₂NHSO₂—, —NHSO₂CH₂—, —SO₂NH—, —CH₂SO₂NH—, —SO₂NHCH₂—, —NHCO—, —CH₂NHCO—, —NHCOCH₂—, —CONH—, —CH₂CONH—, —CONHCH₂—, —OCH₂—, —CH₂OCH₂, —OCH₂CH₂—, —CH₂O— or —CH₂CH₂O—;

R⁶ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, C₁₋₄-alkylamino-C₁₋₄-alkyl, C₁₋₄-dialkylamino-C₁₋₄-alkyl, amino-C₁₋₄-alkyl, C₁₋₄-alkyloxy-C₁₋₄-alkyl, one of the residues (a1) to (a28) or is bonded to one of R⁷, R⁸ or R⁹, if present, with formation of an optionally substituted heterocyclic 4- to 6-membered ring system which includes the nitrogen atom to which R⁶ is bonded and can be saturated or unsaturated and/or can contain further heteroatoms;

X is N, O or S;

R⁷ is absent, is -H, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, —NO₂, —CN, —COR⁷', —COOR⁷' or is bonded to one of R⁶, R⁸ or R⁹ with formation of an optionally substituted carbocyclic or heterocyclic 4- to 6-membered ring system which includes X and can be saturated or unsaturated and/or can contain further heteroatoms;

R⁷' is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof;

R8 is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, C₁₋₄-alkylamino-C₁₋₄-alkyl, C₁₋₄-dialkylamino-C₁₋₄-alkyl, amino-C₁₋₄-alkyl, C₁₋₄-alkyloxy-C₁₋₄-alkyl, one of the residues (a1) to (a28) or is bonded to one of R⁶, R⁷ or R⁹, if present, with formation of an optionally substituted heterocyclic 4- to 6-membered ring system which includes the nitrogen atom to which R⁸ is bonded and can be saturated or unsaturated and/or can contain further heteroatoms; and R⁹ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, C₁₋₄-alkylamino-C₁₋₄-alkyl, C₁₋₄-dialkylamino-C₁₋₄-alkyl, amino-C₁₋₄-alkyl, C₁₋₄-alkyloxy-C₁₋₄-alkyl, one of the residues (a1) to (a28) or is bonded to one of R⁶, R⁷ or R⁸, if present, with formation of an optionally substituted heterocyclic 4- to 6-membered ring system which includes the nitrogen atom to which R⁹ is bonded and can be saturated or unsaturated and/or can contain further heteroatoms.

According to a preferred embodiment, the present invention relates to compounds of the formula (1) in which
R⁴ is —SO₂R⁴';
R⁴' is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C₆H₂(CH₃)₃, —C₆(CH₃)₅, —CH₂C₆H₂(CH₃)₃, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;
L is —NHSO₂—, —CH₂NHSO₂—, —NHSO₂CH₂—;
X is N;
and the other residues are as defined above.

According to a further preferred embodiment, the present invention relates to compounds of the formula (1) in which
R⁴ is —COR⁴';
R⁴' is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C₆H₂(CH₃)₃, —C₆(CH₃)₅, —CH₂C₆H₂(CH₃)₃, 2-chlorophenyl, 3-chlorophenyl, 4-chlorophenyl, 2,3-dichlorophenyl, 2,4-dichlorophenyl, 3,4- dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis (trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)anilin, 4-acetamidophenyl, 2,2,2-trifluoroethyl, 5-chloro-3-methylbenzothiazol-2-yl, N-methoxycarbonylpiperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —NHSO$_2$—, —CH$_2$NHSO$_2$— or —NHSO$_2$CH$_2$—;
X is N;
and the other residues are as defined above.

According to yet a further preferred embodiment, the present invention relates to compounds of the formula (1) in which
R$^4$ is —SO$_2$R$^{4'}$;
R$^{4'}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis (trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)anilin, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —NHCO—, —CH$_2$NHCO— or —NHCOCH$_2$—;
X is N;
and the other residues are as defined above.

According to yet a further preferred embodiment, the present invention relates to compounds of the formula (1) in which
R$^4$ is —SO$_2$R$^4$;
R$^4$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-diclorophenylmethyl, 2,6-dichlorophenylmethyl, 2-methoxycarbonylphenylmethyl, 3-trifluoromethylphenyl, 4-trifluoromethylphenyl, 3,5-bis (trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —OCH$_2$—, —CH$_2$O—, —CH$_2$OCH$_2$—, —CH$_2$CH$_2$O— or —OCH$_2$CH$_2$—;
X is N;
and the other residues are as defined above.

According to yet a further preferred embodiment, the present invention relates to compounds of the formula (1) in which
R$^4$ is —SO$_2$R$^4$;
R$^4$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H,(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis (trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridine-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —NHSO$_2$—, —CH$_2$NHSO$_2$— or —NHSO$_2$CH$_2$—;

X is N;

$R^7$ and $R^9$ together form an ethylene group which bonds the nitrogen atom to which $R^7$ is bonded to the nitrogen atom to which $R^9$ is bonded; and the other residues are as defined above.

The present invention furthermore relates to a process for the preparation of compounds of the formula (1)

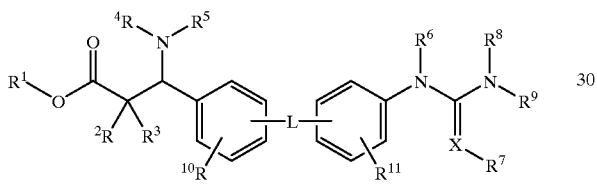

(1)

comprising the steps a) reaction of a β-amino acid of the formula (2)

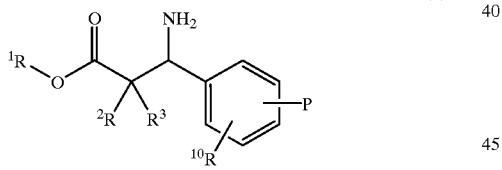

(2)

where

P is —(CH$_2$)$_m$NO$_2$, —(CH$_2$)$_m$O—C$_{1-6}$-alkyl, —(CH$_2$)$_m$SO$_2$P', —(CH$_2$)$_m$COP', —(CH$_2$)$_m$CH$_2$O—C$_{1-6}$-alkyl, where m in each case in an integer of 0 or 1;

P' is —OH, —O—C$_{1-6}$-alkyl, and the other residues are as defined above;

with a compound $R^4$-A to give a compound of the formula (3),

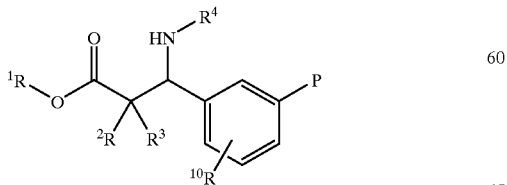

(3)

where $R^4$ is —SO$_2R^{4"}$, —COOR$^{4"}$, or —COR$^{4'}$;

$R^{4'}$ and $R^{4"}$ are as defined above;

A is —Cl, —Br, —I, —O-triflyl, —O-tosyl, —O—C$_{1-6}$-alkyl, —O—CO—C$_{1-6}$-alkyl, —O—CO—O—C$_{1-6}$-alkyl, —OC(CH$_3$)=CH$_2$;

and the other residues are as defined above;

b) conversion of the residue P into the residue Q, where

Q is —(CH$_2$)$_m$NH$_2$, —(CH$_2$)$_m$OH, —(CH$_2$)$_m$CH$_2$OH, —(CH$_2$)$_m$SO$_2$A, —(CH$_2$)$_m$COA,

A is as defined above;

m is an integer of 0 or 1;

c) reaction of the compound obtained from step b) with a compound of the formula (4)

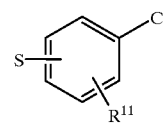

(4)

where

S is ASO$_2$(CH$_2$)$_n$—, NH$_2$(CH$_2$)$_n$—, ACO(CH$_2$)$_n$—, HOCH$_2$(CH$_2$)$_n$—, M(CH$_2$)$_n$—, MCH$_2$ (CH$_2$)$_n$—, HSCH$_2$(CH$_2$)$_n$— or HS(CH$_2$)$_n$—, where n is an integer of 0 or 1;

M is a residue including Mg, Li, Cd or Sn;

A is as defined above; and

C is —NO$_2$ or

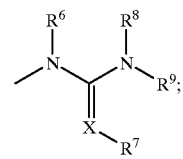

and

X, $R^7$, $R^8$, $R^9$ and $R^{11}$ are as defined above;

to give a compound of the formula (5)

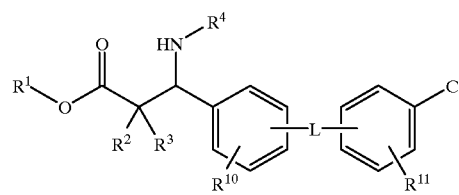

(5)

where the residues are as defined above;

d) if appropriate, conversion of C, if C is a nitro group, into an optionally cyclic urea, thiourea or guanidine unit with obtainment of the compound (1); and e) if appropriate, removal of protective groups and/or derivatization of nitrogen atoms, which are present at preferred times within the preparation process, and/or conversion of the compound obtained into the free acid and/or conversion of the compound obtained into one of its physiologically acceptable salts by reaction with an inorganic or organic base or acid.

Preferably, in the process according to the invention the β-amino acid of the formula (2) is obtained by reaction of malonic acid with a benzaldehyde derivative of the formula (2a)

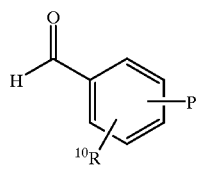

where $R^{10}$ and P are as defined above, in the presence of ammonia, ammonium compounds or amines and, if appropriate, subsequent substitution in the α-position to the terminal carboxyl group.

Furthermore, according to a preferred embodiment of the invention, the process comprises the conversion of the nitro group in step d) by reduction to the amino group, subsequent reaction with a carbonic acid ester derivative and, if appropriate, removal of protective groups present and/or reaction with a compound containing at least one amino group.

The present invention furthermore relates to a pharmaceutical composition which contains at least one of the compounds according to the invention described above.

The present invention furthermore relates to the use of the compounds according to the invention described above for the production of a pharmaceutical composition having integrin-antagonistic action.

The present invention furthermore relates to the use of the compounds according to the invention described above for the production of a pharmaceutical composition for the therapy and prophylaxis of cancer, osteolytic diseases such as osteoporosis, arteriosclerosis, restenosis and ophthalmic disorders.

DETAILED DESCRIPTION OF THE PREFERRED EMBODIMENTS

The invention is explained more exactly below with reference to preferred embodiments to which, however, it is not restricted in any way. In the description below, bivalent substituents are indicated in such a way that their respective left end is connected to the group indicated left of the corresponding substituent in formula (1), and their respective right end is connected to the group indicated right of the corresponding substituent in formula (1). If, for example, the residue L is —$(CH_2)_m$NHSO$_2$$(CH_2)_n$— in formula (1), the nitrogen atom is connected to the phenylene group located left of the residue L in formula (1) by means of the group $(CH_2)_m$.

The compounds according to the invention are characterized in that, as a main structural element, they have two phenyl units connected via a linker group L, one phenylene group of which has the residue derived from a β-amio acid, while the other phenylene group carries a urea group, thiourea group or guanidine group optionally incorporated into a cyclic ring system. The phenylene units bonded by a linker group L can moreover carry further substituents in addition to the abovementioned residues.

The terminal carboxyl unit included in the residue derived from a β-amino acid can be present as a free carboxylic acid or as an ester. In the case in which the terminal carboxyl unit is esterified, basically all carboxylic acid esters obtainable according to conventional processes and which can be metabolized into the free carboxylic acid in the animal body, such as the corresponding alkyl esters, cycloalkyl esters, aryl esters and heterocyclic analogues thereof can be used according to the invention, where alkyl esters, cycloalkyl esters and aryl esters are preferred and the alcoholic residue can carry further substituents. $C_{1-6}$-Alkyl esters such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester are particularly preferred.

The abovementioned esters can be employed as prodrugs for the treatment of the diseases mentioned at the beginning, such as cancer, osteoporosis, arteriosclerosis, restenosis or ophthalmia, since they are easily converted in an animal and in man to the corresponding carboxylic acid. However, for the treatment of the abovementioned disorders the compounds of the general formula (1) according to the invention are preferably used in a form in which the terminal carboxyl unit is present as a free carboxylic acid.

For medicinal use, the compounds of the general formula (1) according to the invention can also be employed in the form of their physiologically acceptable salts. Physiologically acceptable salts are understood according to the invention as meaning non-toxic salts, which in general are accessible by reaction of the compounds of the general formula (1) according to the invention with an inorganic or organic base or acid conventionally used for this purpose. Examples of preferred salts of the compounds of the general formula (I) according to the invention are the corresponding alkali metal salt, e.g. the lithium, potassium or sodium salt, the corresponding alkaline earth metal salt such as the magnesium or calcium salt, a quaternary ammonium salt such as, for example, the triethylammonium salt, acetate, benzenesulphonate, benzoate, dicarbonate, disulphate, ditartrate, borate, bromide, carbonate, chloride, citrate, dihydrochloride, fumarate, gluconate, glutamate, hexylresorcinate, hydrobromide, hydrochloride, hydroxynaphthoate, iodide, isothionate, lactate, laurate, malate, maleate, mandelate, mesylate, methylbromide, methylnitrate, methylsulphate, nitrate, oleate, oxalate, palmitate, pantothenate, phosphate, diphosphate, polygalacturonate, salicylate, stearate, sulphate, succinate, tartrate, tosylate and valerate, and other salts used for medicinal purposes.

The residue bonded to one of the two central phenylene units and derived from a β-amino acid can alternatively carry one or two additional substituents in the α-position to the carboxyl group. These substituents can in each case be selected from the group which consists of hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, a hydroxyl residue or an alkoxy residue. The alkyl residue can preferably be a $C_{1-6}$-alkyl such as, for example, methyl, ethyl, propyl, isopropyl, butyl, isobutyl, t-butyl, pentyl, isopentyl, neopentyl or hexyl. The cycloalkyl residue can preferably be a $C_{3-7}$-cycloalkyl such as, for example, cyclopropyl, cyclopropylmethyl, cyclobutyl, cyclopentyl, cyclohexyl or cycloheptyl. The aryl residue can preferably be phenyl, benzyl or tolyl. The heterocyclic residue can preferably be pyrrole, pyridine, tetrahydrofuran, furan, thiophene, tetrahydrothiophene, thiooxazole, benzofuran, quinoline, isoquinoline or pyrimidine. The alkenyl residue can be a terminal or internal E or Z alkene unit. The alkoxy residue can preferably be a $C_{1-6}$-alkoxy residue such as, for example, methoxy, ethoxy, propoxy, butoxy, pentoxy, hexoxy or benzyloxy. The abovementioned residues can alternatively be substituted by one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl or cyclohexyl, aryl residues such as phenyl, benzyl, tolyl, naphthyl, heterocyclic residues such as pyrrole, pyridine, tetrahydrofuran, furan, thiophene, tetrahydrothiophene, oxazole, thiazole, thiooxazole, benzofuran, benzoxazole, benzothiazole, quinoline, isoquinoline, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. One or more additionally saturated or unsaturated rings can furthermore be fused to the abovementioned cyclic residues with formation of, for example, a naphthyl, benzofuranyl, benzoxazolyl, benzothiazolyl, quinolinyl or isoquinolinyl unit or a partially or completely hydrogenated analogue thereof.

The two substituents in the α-position to the terminal carboxyl group, if present, can furthermore be bonded to one another and can thus together form a carbocyclic or heterocyclic ring system together with the α-carbon atom of the residue derived from a α-amino acid. This ring system can optionally carry further substituents and/or contain further heteroatoms. According to the invention, the above ring system, if present, is preferably a 3- to 6-membered carbocyclic or heterocyclic ring system such as, for example, a cyclopropane ring, cyclobutane ring, cyclopentane ring, cyclohexane ring, dihydrofuran ring, tetrahydrofuran ring, dihydropyran ring, tetrahydropyran ring, dioxane ring, dihydrothiophene ring, tetrahydrothiophene ring or a substituted derivative thereof.

In the groups according to the invention, the amino group included in the residue derived from a β-amino acid is substituted by one of the residues —$SO_2R^4$, —$COOR^{4"}$, —$COR^4$, —$CONR^{4'}_2$ or —$CSNR^{4'}_2$, where $R^{4'}$ can be hydrogen, a substituted or unsubstituted alkyl or cycloalkyl residue, a substituted or unsubstituted aryl residue or a saturated or unsaturated, optionally substituted heterocyclic residue and $R^{4"}$ can be a substituted or unsubstituted alkyl or cycloalkyl residue, a substituted or unsubstituted aryl residue or a saturated or unsaturated, optionally substituted heterocyclic residue. In this context, the alkyl residue is preferably a $C_{1-6}$-alkyl such as, for example, methyl, ethyl, propyl, isopropyl, butyl, isobutyl, t-butyl, pentyl, isopentyl, neopentyl, hexyl, the cycloalkyl residue is a $C_{3-7}$-cycloalkyl such as, for example, cyclopropyl, cyclobutyl, cyclopentyl, cyclohexyl, cycloheptyl, the aryl residue is an aryl such as phenyl, benzyl, tolyl or a substituted derivative thereof such as —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl.

According to the invention, the amino group included in the residue derived from a β-amino acid is particularly preferably substituted by —$SO_2R^{4'}$ or —$COR^{4'}$, where $R^{4'}$ is as defined above. In this context, compounds are particularly preferred in which the residue derived from a β-amino acid has no substituent in the α-position to the carboxyl unit and the amino group included in this residue is substituted by —$SO_2R^4$ or —$COR^{4'}$, where $R^4$ is as defined above.

In addition to one of the abovementioned residues, the nitrogen atom of the amino group situated in the β-position can have a substituent which can be from the group consisting of hydrogen, a substituted or unsubstituted alkyl or cycloalkyl residue, a substituted or unsubstituted aryl residue, a saturated or unsaturated, optionally substituted heterocyclic residue or can be bonded to one another and can thus form a heterocyclic ring system together with the nitrogen atom(s) to which they are bonded. In this context, substituents are preferred which can be selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl, cyclohexyl or cycloheptyl, an aryl such as, for example, phenyl, benzyl or tolyl, a heterocyclic residue such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine and can alternatively be substituted by one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl or cyclohexyl, aryl residues such as phenyl, benzyl, tolyl, naphthyl, indolyl, heterocyclic residues such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. One or more additionally saturated or unsaturated rings can furthermore be fused to the abovementioned cyclic residues with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof. Particularly preferably, the additional substituent on the nitrogen atom of the β-amino group is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methyl-cyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl,

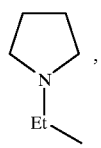 (a1)

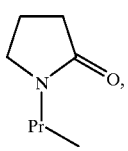 (a2)

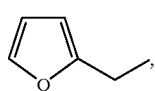 (a3)

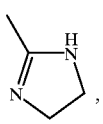 (a4)

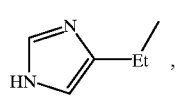 (a5)

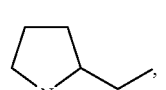 (a6)

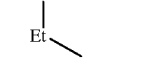 (a7)

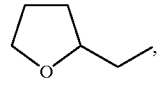 (a8)

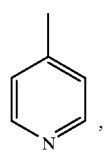 (a9)

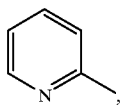 (a10)

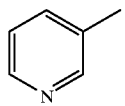 (a11)

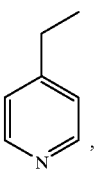 (a12)

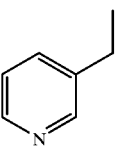 (a13)

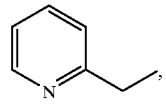 (a14)

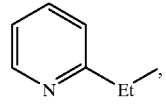 (a15)

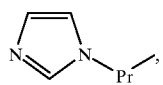 (a16)

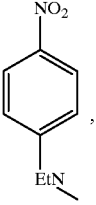 (a17)

(a18) 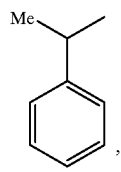

(a19) 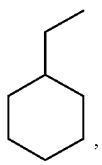

(a20) 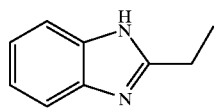

(a21) 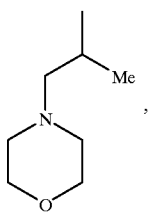

(a22) 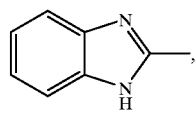

(a23) 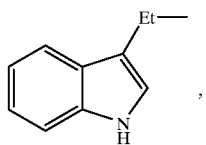

(a24) 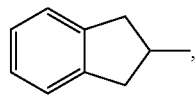

(a25) 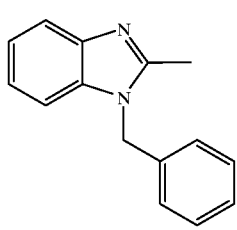

(a26) 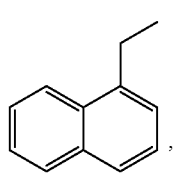

(a27) 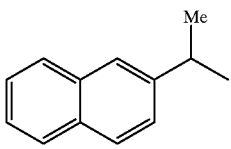

(a28) 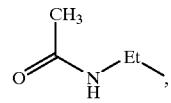

The residue derived from a β-amino acid is bonded to one of the two central phenylene units which are bonded via a linker group L, and that phenylene unit will here be referred to as phenylene unit A. Apart from the residue derived from a β-amino acid and the linker group L, preferably the phenylene unit A carries no further substituents, but can contain one or more residues which are selected from the group consisting of hydrogen, a substituted or unsubstituted alkyl or cycloalkyl residue, a substituted or unsubstituted alkoxy residue or a halogen atom. The alkyl residue(s) are preferably $C_{1-6}$-alkyl residues such as methyl, ethyl, propyl, isopropyl, butyl, isobutyl, t-butyl, pentyl, isopentyl, neopentyl, hexyl. The cycloalkyl residue(s) are preferably $C_{3-7}$-cycloalkyl residues such as cyclopropyl, cyclobutyl, cyclopentyl, cyclohexyl, cycloheptyl. The alkoxy residue(s) are preferably $C_{1-6}$-alkoxy residues such as methoxy, ethoxy, propoxy, butoxy, pentoxy or hexoxy, and the halogen atom(s) are preferably F, Cl, Br or I.

The phenylene unit A is bonded to a second central phenylene unit, which will here be referred to as phenylene unit B, via a linker group L. In addition to the linker group L, the phenylene unit B carries a further substituent which is selected from the group consisting of a guanidine, urea or thiourea unit which is optionally incorporated into a cyclic ring system. Moreover, the phenylene unit B preferably carries no further substituents, but can contain one or more residues which are selected from the group consisting of hydrogen, a substituted or unsubstituted alkyl or cycloalkyl residue, a substituted or unsubstituted alkoxy residue or a halogen atom. The alkyl residue(s) are preferably $C_{1-6}$-alkyl residues such as methyl, ethyl, propyl, isopropyl, butyl, isobutyl, t-butyl, pentyl, isopentyl, neopentyl, hexyl. The cycloalkyl residue(s) are preferably $C_{3-7}$-cycloalkyl residues such as cyclopropyl, cyclobutyl, cyclopentyl, cyclohexyl, cycloheptyl. The alkoxy residue(s) are preferably $C_{1-6}$-alkoxy residues such as methoxy, ethoxy, propoxy, butoxy, pentoxy or hexoxy, and the halogen atom(s) are preferably F, Cl, Br or I.

The two central phenylene units can be 1,3- or 1,4-linked with respect to the linker group L and the residue derived from a β-amino acid or the guanidine, urea or thiourea unit, i.e. the residue derived from a β-amino acid and the linker group L can be substituted on the phenylene unit A in the meta- or para-position to one another, and at the same time the linker group L and the guanidine, urea or thiourea unit on the phenylene unit B can be substituted in the meta- or para-position to one another, where each combination of the abovementioned substitution patterns is possible for the central phenylene A-linker L-phenylene B unit of the compounds according to the invention. According to the present invention, compounds are particularly preferred whose central phenylene A-linker L-phenylene B unit according to the above definition consists of a p-substituted phenylene unit A and a p-substituted phenylene unit B, a p-substituted phenylene unit A and an m-substituted phenylene unit B, an m-substituted phenylene unit A and a p-substituted phenylene unit B or an m-substituted phenylene unit A and an m-substituted phenylene unit B. According to the present invention, compounds are particularly preferred whose central phenylene A-linker L-phenylene B unit according to the above definition consists of an m- substituted phenylene unit A and an m-substituted phenylene unit B. According to the present invention, the linker group L is selected from the group which consists of the elements —$(CH_2)_m NHSO_2 (CH_2)_n$—, —$(CH_2)_m SO_2 NH(CH_2)_n$—, —$(CH_2)_m NHCO (CH_2)_n$—, —$(CH_2)_m CONH(CH_2)_n$—, —$(CH_2)_m OCH_2 (CH_2)_n$—, —$(CH_2)_m CH_2 O(CH_2)_n$—, —$(CH_2)_m COO (CH_2)_n$—, —$(CH_2)_m OOC(CH_2)_n$—, $(CH_2)_m CH_2 CO (CH_2)_n$—, —$(CH_2)_m COCH_2(CH_2)_n$—, —NHCONH—, —$(CH_2)_m\ SCH_2(CH_2)_n$—, —$(CH_2)_m CH_2 S(CH_2)_n$—, —$(CH_2)_m\ CH_2 SO(CH_2)_n$—, —$(CH_2)_m SOCH_2(CH_2)_n$, —$(CH_2)_m\ CH_2 SO_2(CH_2)_n$— or —$(CH_2)_m SO_2 CH_2 (CH_2)_n$—, where m and n in each case are an integer of 0 or 1 and m+n is $\leq 1$.

According to the invention, the linker group L is preferably —$NHSO_2$—, —$CH_2 NHSO_2$—, —$NHSO_2 CH_2$—, —$SO_2 NH$—, —$CH_2 SO_2 NH$—, —$SO_2 NHCH_2$—, —$NHCO$—, —$CH_2 NHCO$—, —$NHCOCH_2$—, —$CONH$—, —$CH_2 CONH$—, —$CONHCH_2$—, —$OCH_2$—, —$CH_2 OCH_2$, —$OCH_2 CH_2$, —$CH_2 O$—, —$CH_2 CH_2 O$—, —$COO$—, —$CH_2 COO$—, —$COOCH_2$—, —$OOC$—, —$OOCCH_2$—, —$CH_2 OOC$—, —$CH_2 CO$—, —$COCH_2$—, —$CH_2 CH_2 CO$—, —$COCH_2 CH_2$—, —$CH_2 COCH_2$—, —NHCONH—, —$SCH_2$—, —$CH_2 S$—, —$CH_2 SCH_2$, —$SCH_2 CH_2$—, $CH_2 CH_2 S$—, —$SOCH_2$—, —$CH_2 SO$—, —$CH_2 SOCH_2$—, —$SOCH_2 CH_2$—, —$CH_2 CH_2 SO$—, —$SO_2 CH_2$—, —$CH_2 SO_2$—, —$CH_2 SO_2 CH_2$—, —$CH_2 CH_2\ SO_2$— or —$SO_2 CH_2 CH_2$—. Particularly preferred linker groups L here are —$NHSO_2$—, —$CH_2 NHSO_2$—, —$NHSO_2 CH_2$—, —$SO_2 NH$—, —$CH_2 SO_2 NH$—, —$SO_2 NHCH_2$—, —$NHCO$—, —$CH_2 NHCO$—, —$NHCOCH_2$—, —$CONH$—, —$CH_2 CONH$—, —$CONHCH_2$—, —$OCH_2$—, —$CH_2 OCH_2$, —$OCH_2 CH_2$—, —$CH_2 O$— or —$CH_2 CH_2 O$—.

The central phenylene unit B carries as a substituent a residue which is selected from the group consisting of a guanidine, urea or thiourea unit. This guanidine, urea or thiourea unit can either be open-chained or a constituent of a cyclic system. The two nitrogen atoms of the respective unit, which are only bonded via single bonds, can carry additional substituents $R^6$, $R^8$ and $R^9$. These substituents can independently of one another or simultaneously be hydrogen, a substituted or unsubstituted alkyl or cycloalkyl residue, a substituted or unsubstituted aryl residue, a saturated or unsaturated, optionally substituted heterocyclic residue or can be bonded to one another and can thus form a heterocyclic ring system together with the nitrogen atom(s) to which they are bonded. In this context, preferred substituents are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl, cyclohexyl or cycloheptyl, an aryl such as, for example, phenyl, benzyl or tolyl, a heterocyclic residue such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine and can alternatively be substituted by one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl or cyclohexyl, aryl residues such as phenyl, benzyl, tolyl, naphthyl, indolyl, heterocyclic residues such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. One or more additionally saturated or unsaturated rings can furthermore be fused to the abovementioned cyclic residues with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof. Particularly preferred are substituents such as hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$- alkyl, amino-$C_{1-4}$-alkyl, $C_{1-4}$-alkyloxy-$C_{1-4}$-alkyl or one of the abovementioned residues (a1) to (a28).

The two residues $R^8$ and $R^9$ on the terminal nitrogen atom of the corresponding guanidine, urea or thiourea unit can be bonded to one another and thus, with the nitrogen atom, form a heterocyclic system which can be selected, for example, from the following, non-conclusive list:

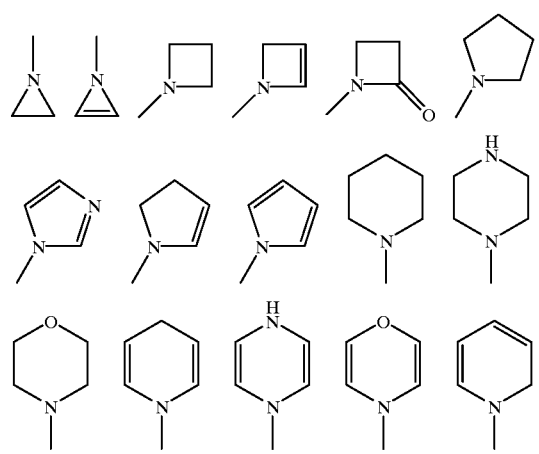

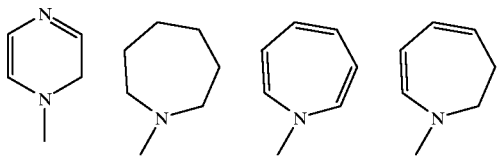

where the ring systems shown can carry one or more residues which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic residue such as, for example, pyrrolidine, piperidine, piperazine, pyrrole, pyridine, tetrahydrofuran, furan, thiophene, tetrahydrothiophene, imida-zolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E or Z alkene unit, and can alternatively be substituted by one or more $C_{1-6}$-alkyl residues such as methyl, ethyl, propyl, isopropyl, butyl, isobutyl, t-butyl, pentyl, isopentyl, neopentyl or hexyl, $C_{3-7}$-cycloalkyl residues such as cyclopropyl, cyclopropylmethyl, cyclobutyl, cyclopentyl or cyclohexyl, aryl residues such as phenyl, benzyl, tolyl, naphthyl, indolyl, heterocyclic residues such as pyrrolidine, piperidine, piperazine, pyrrole, pyridine, tetrahydrofuran, furan, thiophene, tetrahydrothiophene, imida-zolidine, imidazole, oxazolidine, oxazole, thiazolidine, thiazole, thiooxazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. One or more additionally saturated or unsaturated rings can furthermore be fused to the above-mentioned cyclic residues with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof.

Of the ring systems shown above, the four- to six-membered ring systems are preferred.

As mentioned above, the urea, thiourea or guanidine unit can be open-chained or incorporated into a cyclic system and can thus be a constituent of one of the following preferred functional units:

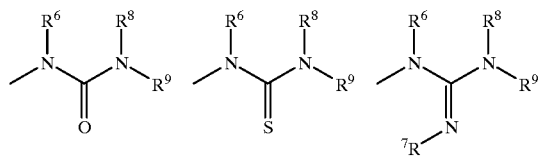

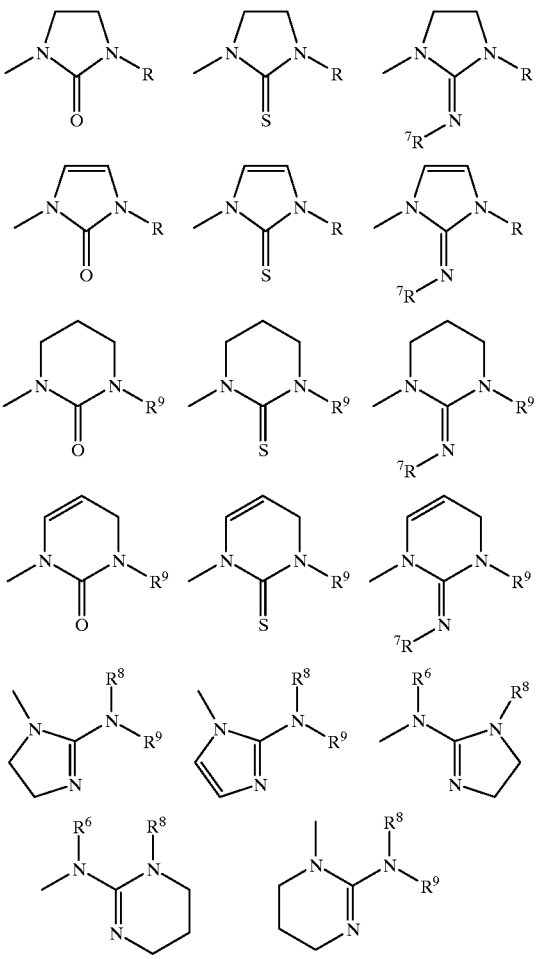

where the above list is not a conclusive enumeration of all possible structural units.

According to the invention, in addition to the abovementioned preferred structural units, their analogues are also included in which one or more 4- to 6-membered ring systems are fused to the heterocycle, such as, for example, the corresponding benzofused analogues of the abovementioned structural units.

In the structural units shown above, $R^6$, $R^8$ and $R^9$ are as defined above.

Furthermore, in the above structural units $R^7$ can be absent, or can be hydrogen, a substituted or unsubstituted alkyl or cycloalkyl residue such as, for example, a $C_{1-6}$-alkyl such as methyl, ethyl, propyl, isopropyl, butyl, isobutyl, t-butyl, pentyl, isopentyl, neopentyl, hexyl or a $C_{3-7}$-cycloalkyl such as cyclopropyl, cyclobutyl, cyclopentyl, cyclohexyl, —$NO_2$, —CN, —$COR^7$ or —$COOR^7$, where $R^7$ can be hydrogen, a substituted or unsubstituted alkyl or cycloalkyl residue, a substituted or unsubstituted aryl residue or a saturated or unsaturated, optionally substituted heterocyclic residue, which can be saturated or unsaturated and/or can contain further heteroatoms, and is preferably a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, an aryl such as, for example, phenyl, benzyl, tolyl, or a substituted derivative thereof Particularly preferred compounds of the formula (1) according to the invention are those in which the amino group included in the residue derived from a β-amino acid carries a residue —SO$_2$R$^4$, where R$^4$ is preferably methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methylbenzothiazole-2-yl, N-methoxycarbonylpiperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl, the linker group L is —NHSO$_2$—, —CH$_2$NHSO$_2$—, —NHSO$_2$CH$_2$—, and the residue located on the phenylene unit is an open-chain or cyclic guanidine unit, where a cyclic guanidine unit such as, for example, a 4,5-dihydro-1H-imidazol-2-yl-amino unit is particularly preferred.

Furthermore, particularly preferred compounds of the formula (1) according to the present invention are those in which the amino group included in the residue derived from a β-amino acid carries a residue —SO$_2$R$^{4'}$, where R$^{4'}$ is preferably methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl, the linker group L is —NHCO—, —CH$_2$NHCO—, —NHCOCH$_2$— or —OCH$_2$—, —CH$_2$O—, —CH$_2$OCH$_2$—, —CH$_2$CH$_2$O—, —OCH$_2$CH$_2$—, and the residue located on the phenylene unit is an open-chain or cyclic guanidine unit, where a cyclic guanidine unit such as, for example, a 4,5-dihydro-1H-imidazol-2-yl-amino unit is particularly preferred.

Moreover, particularly preferred compounds of the formula (1) according to the present invention are those in which the amino group included in the residue derived from a β-amino acid carries a residue —COR$^{4'}$, where R$^{4'}$ is preferably hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propyl-phenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methyphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetarnidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl, the linker group L is —NHSO$_2$—, —CH$_2$NHSO$_2$—, —NHSO$_2$CH$_2$—, and the residue located on the phenylene unit is an open-chain or cyclic guanidine unit, where a cyclic guanidine unit such as, for example, a 4,5-dihydro-1H-imidazol-2-yl-amino unit is particularly preferred.

The present invention comprises both the individual enantiomers or diastereomers and the corresponding racemates, diastereomer mixtures and salts of the compounds defined in claim 1. In addition, according to the present invention all possible tautomeric forms of the compounds described above are also included. The present invention furthermore comprises the pure E and Z isomers of the compounds of the general formula (1) and their E/Z mixtures in all ratios. The diastereomer mixtures or E/Z mixtures can be separated into the individual isomers by chromatographic procedures. The racemates can be separated into the respective enantiomers either by chromatographic procedures on chiral phases or by resolution.

The compounds described above can be prepared from commercially available starting compounds. The main steps of the preparation process according to the invention are the reaction of a β-amino acid of the formula (2)

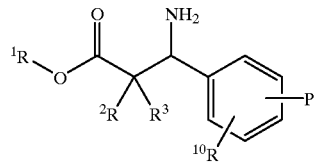
(2)

where

P is —$(CH_2)_mNO_2$, —$(CH_2)_mO$-$C_{1-6}$-alkyl, —$(CH_2)_m SO_2P'$, —$(CH_2)_mCOP'$, —$(CH_2)_mCH_2O$-$C_{1-6}$-alkyl, where m in each case is an integer of 0 or 1;
P' is —OH, —O—$C_{1-6}$-alkyl,
and the other residues are as defined above;

with a compound $R^4$-A to give a compound of the formula (3),

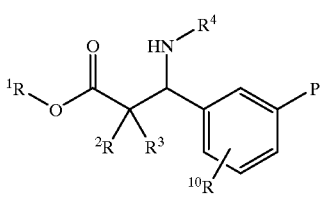
(3)

where $R^4$ is —$SO_2R^{4'}$, —$COOR^{4''}$, or —$COR^{4'}$; $R^{4'}$ and $R^{4''}$ are as defined above; A is —Cl, —Br, —I, —O-triflyl, —O-tosyl, —O—$C_{1-6}$-alkyl, —O—CO—$C_{1-6}$-alkyl, —O—CO—O—$C_{1-6}$-alkyl, —$OC(CH_3)$=$CH_2$; and the other residues are as defined above;
the conversion of the residue P into the residue Q, where Q is —$(CH_2)_mNH_2$, —$(CH_2)_mOH$, —$(CH_2)_mCH_2OH$, —$(CH_2)_mSO_2A$, —$(CH_2)_mCOA$, A is as defined above; m is an integer of 0 or 1;

the reaction of the compound (3) obtained above with a compound of the formula (4)

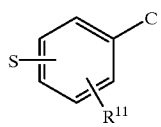
(4)

where S is $ASO_2(CH_2)_n$—, $NH_2(CH_2)_n$—, $ACO(CH_2)_n$—, $HOCH_2(CH_2)_n$—, $M(CH_2)_n$—, $MCH_2(CH_2)_n$—, $HSCH_2(CH_2)_n$— or $HS(CH_2)_n$—, where n is an integer of 0 or 1; M is a residue including Mg, Li, Cd or Sn; A is as defined above; and C is —$NO_2$ or

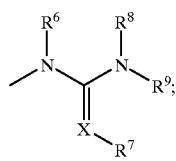

and
X, $R^7$, $R^8$, $R^9$ and $R^{11}$ are as defined above;
to give a compound of the formula (5)

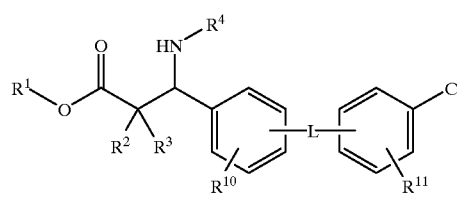
(5)

where the residues are as defined above;
if appropriate the conversion of C, if C is a nitro group, into an optionally cyclic urea, thiourea or guanidine unit with obtainment of the compound (1); and
if appropriate the removal of protective groups and/or derivatization of nitrogen atoms, which are present, at preferred times within the preparation process, and/or conversion of the compound obtained into the free acid and/or conversion of the compound obtained into one of its physiologically acceptable salts by reaction with an inorganic or organic base or acid.

The β-amino acid derivatives of the formula (2) are either commercially available or are accessible in a simple manner by standard chemical processes, such as are known to any person skilled in the art and described in standard works such as Houben- Weyl, Methoden der organischen Chemie [Methods of Organic Chemistry], Georg Thieme-Verlag, Stuttgart. In particular, reference is made to the preparation process for β-amino acid derivatives described by Rodionow et al., J. Am. Chem. Soc. 51, 1929, 844–846, Kunz et al., Angew. Chem. 101, 1989, 1042–1043 and Ishihara et al., Bull. Chem. Soc. Jpn., 68, 6, 1995, 1721–1730.

According to a preferred embodiment of the present invention, the β-amino acid derivatives of the formula (2) are obtained by reaction of malonic acid with a benzaldehyde derivative of the formula (2a)

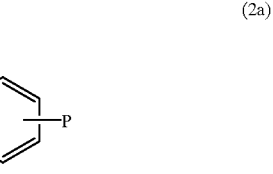
(2a)

where $R^{10}$ and P are as defined above, in the presence of ammonia, ammonium compounds or amines. Instead of malonic acid, an ester can also be used, if appropriate with addition of a base conventionally employed for these purposes, such as NaH or a sodium alkoxide, preferably sodium methoxide or sodium ethoxide. An ammonium compound such as, for example, ammonium acetate is preferably employed as the nitrogen compound.

The benzaldehyde derivatives (2a) are either commercially available or are accessible in a simple manner by standard chemical processes, such as are known to any person skilled in the art and described in standard works such as Houben-Weyl, Methoden der organischen Chemie [Methods of Organic Chemistry], Georg Thieme-Verlag, Stuttgart.

According to a preferred embodiment of the present invention, the compound of the formula (2a) employed is a nitrobenzaldehyde derivative such as 3- or 4-nitrobenzaldehyde or an alkoxybenzaldehyde derivative such as 3- or 4-methoxybenzaldehyde.

According to a preferred embodiment of the present invention, the β-amino acid of the formula (2) is obtained by reaction of approximately equimolar amounts of malonic acid, ammonium acetate and 3-nitrobenzaldehyde or 3-methoxybenzaldehyde in a solvent such as isopropanol with heating at 50 to 110° C. for several hours, preferably 2 to 6 hours, preferably under reflux of the solvent, in the surrounding atmosphere (i.e. in the air and under normal pressure).

For the following reaction steps, the carboxyl group is blocked by a conventional protective group P. Protective groups of this type are known to the person skilled in the art and do not expressly need to be mentioned here. Particularly preferably, the carboxyl group is esterified, P being a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclopropylmethyl, cyclobutyl, cyclopentyl, cyclohexyl, an aryl such as, for example, phenyl, benzyl or tolyl or a substituted derivative thereof. Furthermore, the preparation process according to the invention for the compounds of the general formula (1) can be carried out on a solid phase. In this case the carboxyl residue can be bonded to any solid phase conventionally used for reactions of this type, such as a polystyrene resin, for example a Wang polystyrene resin.

According to a preferred embodiment according to the invention, the carboxyl group of the above β-amino acid is esterified by reaction with an alcohol such as ethanol. This can be carried out under conditions known to the person skilled in the art, such as acid catalysis and, if appropriate, addition of a dehydrating agent such as dicyclohexylcarbodiimide. Preferably, however, the β-amino acid is suspended in the appropriate alcohol, such as ethanol, which is present in excess, HCl is passed in over a period of approximately 30 minutes to approximately 2 hours and the mixture is then heated in a surrounding atmosphere for several hours, preferably approximately 1 to 6 hours and particularly preferably approximately 3 to 5 hours, at approximately 50 to approximately 100° C., preferably under reflux of the alcohol.

The carboxyl-protected β-amino acids thus accessible are reacted with a suitable sulphonylating, carbamoylating or acylating reagent in order to obtain the corresponding sulphonamide, carbamate or amide derivatives. The sulphonating reagent preferably used is a sulphonyl chloride of the formula $R^{4''}$—$SO_2Cl$ or a carbamoyl chloride of the formula $R^{4'}$-OCOCl, where $R^{4''}$ is a $C_{1-10}$-alkyl such as methyl, ethyl, propyl, isopropyl, butyl, isobutyl, t-butyl, pentyl, isopentyl, neopentyl, hexyl, heptyl, octyl, nonyl, decyl, cyclopropyl, cyclobutyl, cyclopentyl, cyclohexyl, or camphor-10-yl, an aryl such as phenyl, benzyl, tolyl, mesityl or substituted derivatives of these such as —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl, 8-quinolinyl, or a heterocyclic analogue of the abovementioned cyclic residues. Instead of the abovementioned sulphonyl or carbamoyl chlorides, the corresponding fluorides, bromides or iodides can also be employed. As an acylating reagent, the appropriate carbonyl halides or carboxylic anhydrides are reacted with the amino group, where the appropriate $C_{1-6}$-alkyl chlorides such as methyl chloride, ethyl chloride, propyl chloride, isopropyl chloride, butyl chloride, isobutyl chloride, t-butyl chloride, pentyl chloride, isopentyl chloride, neopentyl chloride, hexyl chloride, $C_{3-7}$-cycloalkyl chlorides such as cyclopropyl chloride, cyclobutyl chloride, cyclopentyl chloride, cyclohexyl chloride, aryl chlorides such as phenyl chloride, benzyl chloride, tolylcarboxylic acid chlorides or substituted derivatives thereof are preferred according to the invention. For the preparation of the urea or thiourea derivatives, the amino group is preferably first reacted with a carbonic acid or thiocarbonic acid derivative such as a chloroformic acid ester or thiophosgene and then with a desired amine. The above reactions and their implementation are well known to the person skilled in the art and described in detail in standard works such as, for example, Houben-Weyl, Methoden der organischen Chemie [Methods of Organic Chemistry], Georg Thieme Verlag, Stuttgart.

According to a preferred embodiment of the invention, the carboxyl-protected β-amino acid of the formula (2) is treated with an equimolar amount or a slight excess of the appropriate sulphonylating agent, for example phenylsulphonyl chloride, or acylating agent, for example mesitylacetyl chloride, with cooling, preferably at 0° C., in a solvent such as pyridine or dioxane in a surrounding atmosphere in the presence of a base such as an amine, preferably triethylamine or diisopropylethylamine, and stirred at this temperature for a period of approximately 10 minutes to approximately 2 hours. In the case of sulphonylation, stirring at room temperature for several hours, preferably approximately 2 to 6 hours, follows this.

Before the construction of the linker group L, the residue P of the compound of the formula (3) must be converted into a group Q which can participate in a nucleophilic substitution either as a nucleophilic reagent or as a substrate. If P includes a nitro group, this is reduced to the corresponding amino group, which reduction can be carried out according to the present invention preferably by addition of tin-(II)

chloride to a solution of the compound of the formula (3) in a solvent such as ethanol and subsequent heating to approximately 50 to 110° C., preferably under reflux of the solvent, for several hours, preferably approximately 1 to 4 hours, in a surrounding atmosphere. If P includes an ether group, the liberation of the corresponding hydroxyl group is preferably carried out by addition of a Lewis acid such as boron tribromide in a solvent such as dichloromethane with cooling, preferably at −78° C., and subsequent stirring for several hours, preferably 6 to 24 hours, at room temperature. If P includes a sulphonic acid or carboxylic acid group, conversion into the corresponding sulphonyl or carbonyl halide preferably takes place. This can be carried out in a manner known to the person skilled in the art, for example by reaction of the corresponding sulphonic or carboxylic acid with thionyl chloride.

The compound prepared in this way is then reacted with a compound of the formula (4)

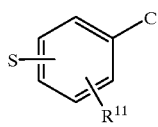

(4)

where

S is $ASO_2(CH_2)_n-$, $NH_2(CH_2)_n-$, $ACO(CH_2)_n-$, $HOCH_2(CH_2)_n-$, $M(CH_2)_n-$, $MCH_2(CH_2)_n-$, $HSCH_2(CH_2)_n-$ or $HS(CH_2)_n-$, where n is an integer of 0 or 1;

M is a residue including Mg, Li, Cd or Sn;

A is as defined above; and

C is $-NO_2$ or

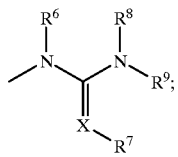

and $X$, $R^7$, $R^8$, $R^9$ and $R^{11}$ are as defined above;

to give a compound of the formula (5)

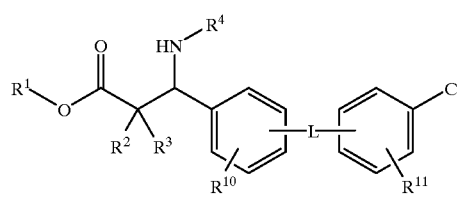

(5)

where the residues are as defined above. This reaction formally represents the substitution of a leaving group in one of the starting compounds by a nucleophilic unit in the other starting compound in each case.

According to a preferred embodiment of the present invention, the reactants are mixed together in approximately equimolar amounts in the presence of a base such as pyridine or sodium hydride and optionally in a solvent such as, for example, tetrahydrofuran (THF) or dimethylformamide (DMF) in a surrounding atmosphere at room temperature or with cooling, preferably at approximately 0° C., and stirred for several hours, preferably approximately 1 h to approximately 24 hours, at room temperature or with cooling, for example at 0° C.

The compounds of the formula (5) thus obtained are converted into the compounds of the formula (1) according to the invention by conversion of the terminal nitro group into an open-chain or cyclic guanidine, urea or thiourea unit.

For this purpose, the nitro group is first preferably converted according to the invention into an amino group by addition of a customary reducing agent such as tin- (II) chloride, if appropriate in the presence of solvents such as ethanol, by stirring the reaction mixture with heating to approximately 50 to 110° C., preferably under reflux of the solvent, in a surrounding atmosphere for approximately 2 hours.

The amino group thus obtained is then converted into a guanidine, urea or thiourea unit. For this purpose, the above amino group is preferably first reacted with a carbonic acid ester or thiocarbonic acid ester derivative in a solvent such as dimethyl- formamide (DMF) in the presence of mercury- (II) chloride with cooling, preferably at approximately 0° C., and stirring for approximately 10 minutes for up to approximately 3 hours with cooling, preferably at approximately 0° C., and if appropriate then at room temperature. The carbonic acid ester or thiocarbonic acid ester derivative employed can preferably be phosgene, triphosgene, thiophosgene, chloroformic acid esters or thiopseudourea derivatives, commercially available chloroformic acid esters being preferred for the preparation of the urea derivatives, thiophosgene being preferred for the preparation of the thiourea derivatives and thiopseudourea derivatives being preferred for the preparation of the guanidine derivatives.

The carbamates or isothiocyanates formed in this way can be converted into the corresponding urea, thiourea and guanidine derivatives by reaction with appropriate amines. Amines which can be used are substances of the formula HNRR', where R and R' independently of one another or simultaneously are hydrogen, a substituted or unsubstituted alkyl or cycloalkyl residue, a substituted or unsubstituted aryl residue, a saturated or unsaturated, optionally substituted heterocyclic residue, an alkylamine residue, an alkylamide residue or are bonded to one another and together with the nitrogen atom can form an optionally substituted heterocyclic ring system which can be saturated or unsaturated and/or can contain further heteroatoms. With respect to the preferred residues on the amine, reference is made to the above description of the compounds according to the invention. According to the invention, the carbamate or isothiocyanate is preferably reacted with an amine at room temperature with stirring for approximately 1 to 5 hours, preferably approximately 2 to 3 hours, in the presence of an auxiliary base such as diisopropylethylamine in a solvent such as dimethylformamide (DMF). In the case of the preparation of cyclic guanidine derivatives, the corresponding isothiocyanate is preferably first heated in ethanol for several hours, preferably approximately 12 to 24 hours, and then heated with a diamine such as diaminoethane in a solvent such as toluene, dimethylformamide (DMF) or a mixture of the two.

According to a further preferred embodiment of the present invention, it is also possible to generate the above guanidine, urea or thiourea group in the above manner initially on the compound of the formula (4) and to react the compound of the formula (4) thus obtained subsequently in the manner described above with the compound of the formula (3).

The compounds obtained according to the processes explained above can furthermore be derivatized by removal of protective groups which may be present, continued substitution of nitrogen atoms, which are present, at preferred positions in the preparation process, and/or conversion of the compound obtained into the free acid and/or its physiologically acceptable salts. For example, the t-butoxymethoxycarbonyl groups conventionally used as a protective group for nitrogen atoms are removed in an acidic medium, for example by addition of trifluoroacetic acid. Possible alkylating agents for the derivatization of nitrogen atoms are reagents conventionally used for this purpose in this step, with which, for example, a substituted or unsubstituted alkyl or cycloalkyl residue, a substituted or unsubstituted aryl residue or a saturated or unsaturated, optionally substituted heterocyclic residue can be bonded to the appropriate nitrogen atom. With respect to the substituents preferably bonded to the respective nitrogen atoms, reference is made to the above description of the compounds according to the invention. The above reactions and their implementation are well known to the person skilled in the art and described in detail in standard works such as, for example, Houben-Weyl, Methoden der organischen Chemie [Methods of Organic Chemistry], Georg Thieme Verlag, Stuttgart.

The ester derivatives according to the invention can be converted into the corresponding free carboxylic acids in a customary manner, such as, for example, by basic ester hydrolysis.

If desired, the compounds according to the invention can be converted into their physiologically acceptable salts. This can be effected either by reaction with an organic or inorganic base such as, for example, an alkali metal hydroxide or alkaline earth metal hydroxide such as KOH, NaOH, LiOH, Mg(OH)$_2$ or Ca(OH)$_2$, as a result of which the terminal carboxyl group is deprotonated and the corresponding carboxylate is formed, or by reaction with an organic or inorganic acid such as, for example, hydrochloric acid, sulphuric acid, phosphoric acid, mandelic acid, oleic acid, linoleic acid or p-toluenesulphonic acid, as a result of which one or more of the nitrogen atoms present are protonated.

The steps of the preparation process according to the invention described above can be carried out in a normal atmosphere, i.e. in air, and without the use of absolute, i.e. essentially anhydrous, solvents.

The compounds according to the invention exhibit a very good antagonistic action against integrin receptors, in particular the $\alpha_v\beta_3$ receptor or the $\alpha_v\beta_5$ receptor. This makes them suitable for use as pharmaceutical compositions, in particular for the treatment and prophylaxis of arteriosclerosis, restenosis, osteolytic disorders such as osteoporosis, cancer and ophthalmic diseases.

The compounds according to the invention can be used as active compound components for the production of pharmaceutical compositions against the abovementioned diseases. For this purpose, they can be converted into the customary formulations such as tablets, coated tablets, aerosols, pills, granules, syrups, emulsions, suspensions and solutions using inert, non-toxic, pharmaceutically suitable excipients or solvents. The compounds according to the invention are preferably used here in such an amount that their concentration in the total mixture is approximately 0.5 to approximately 90% by weight, the concentration being dependent, inter alia, on the corresponding indication of the pharmaceutical composition.

The abovementioned formulations are prepared, for example, by extending the active compounds using solvents and/or excipients having the above properties, where, if appropriate, emulsifying agents or dispersing agents, and, in the case of water as a solvent, alternatively an organic solvent additionally has to be added.

The pharmaceutical compositions according to the invention can be administered in a customary manner.

The present invention is illustrated below with the aid of non-restricting examples and comparison examples.

EXAMPLES

In the examples below, all quantitative data relate, unless stated otherwise, to percentages by weight. The mass determinations were carried out by high-performance liquid chromatography-mass spectrometry (HPLC-MS) using the electron spray ionization (ESI) method.

Example 1

General synthesis scheme:

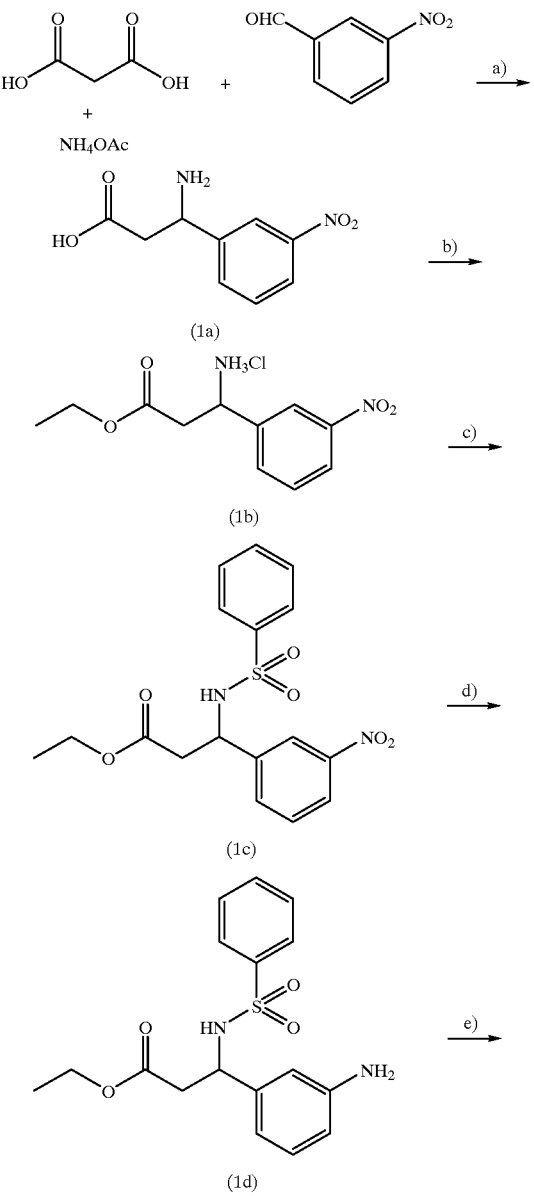

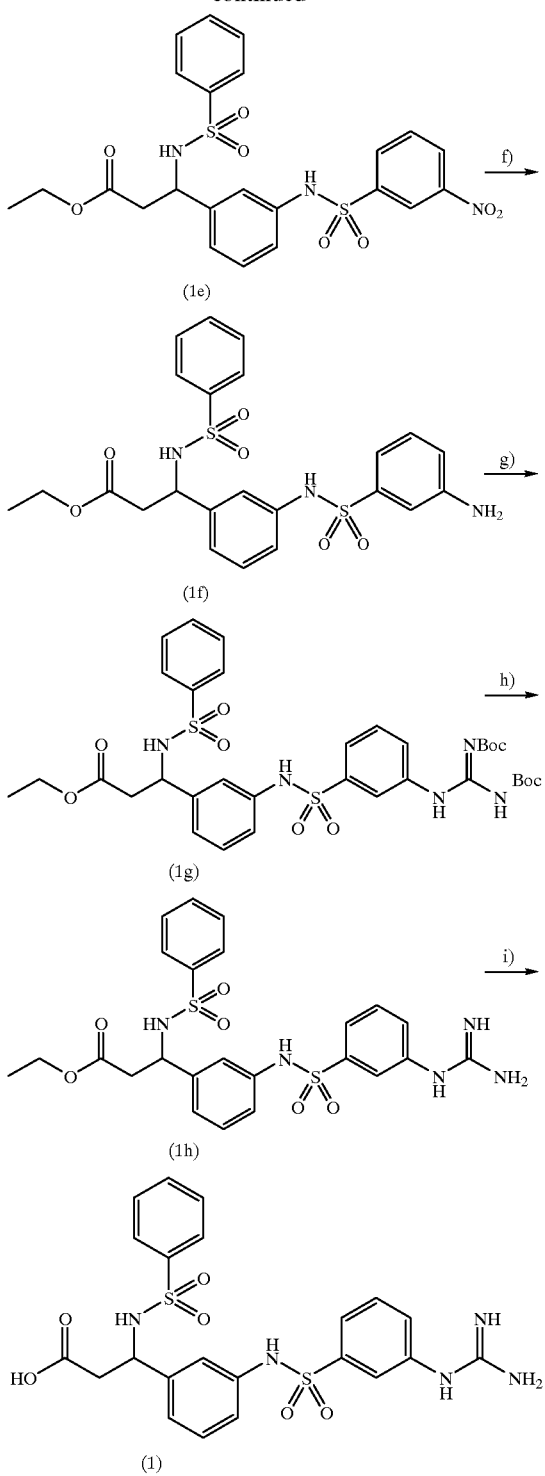

(1e)

(1f)

(1g)

(1h)

(1)

a) 2-propanol, reflux; b) HCl, ethanol; c) PhSO$_2$Cl, Et$_3$N; d) SnCl$_2$, ethanol; e) 3-NO$_2$-C$_6$H$_4$SO$_2$Cl; f) SnCl$_2$, ethanol; g) HgCl$_2$, 1,3-bis(tert-butyloxycarbonyl)-2-methyl-2-thiopseudourea; h) TFA, dichloromethane, i) LiOH.

3-Amino-3-(3-nitrophenyl)-propionic acid hydrochloride (1a)

151 g of 3-nitrobenzaldehyde, 94 g of ammonium acetate and 127 g of malonic acid were heated under reflux for 5 h in 1 l of isopropanol. The solution was filtered and the precipitate was washed with 0.7 l of hot isopropanol. The crude product was dried in vacuo, suspended in 1.5 l of water, treated with hydrochloric acid and filtered, and the filtrate was concentrated (yield: 146 g). 1H), 8.33 (d, 1H), 8.43 (s, 1H).

Ethyl 3-amino-3-(3-nitrophenyl)-propionate hydrochloride (1b)

60 g of (1a) were suspended in 660 ml of ethanol, and gaseous HCl was passed in for 1 h. The reaction mixture was then heated under reflux for 4 h and then cooled and concentrated. 62 g of a white solid were obtained.

$^1$H-NMR (400 MHz, D$_4$-MeOH): 1.22 (t, 3H), 3.12 (dd, 1H), 3.20 (dd, 1H), 4.18 (q, 2H), 4.95 (t, 1H), 7.77 (t, 1H), 7.94 (d, 1H), 8.35 (d, 1H), 8.43 (s, 1H).

Ethyl 3-benzenesulphonylamino-3-(3-nitrophenyl)-propionate (1c)

8.1 g of phenylsulphonyl chloride were added at 0° C. to a solution of 10 g of (1b) in 100 ml of pyridine. After a reaction time of 15 min, 6.3 ml of triethylamine were added and the mixture was stirred at room temperature. After 5 h, it was concentrated, treated with 1 N HCl, extracted with dichloromethane, dried over MgSO$_4$ and concentrated. Chromatographic purification (dichloromethane/methanol= 5:1) yielded 11.4 g of a white solid.

$^1$H-NMR (400 MHz, CDCl$_3$): 1.16 (t, 3H), 2.80 (m, 2H), 4.05 (q, 2H), 4.87 (q, 1H), 6.06 (d, 1H), 7.35–7.50 (m, 5H), 7.71 (d, 2H), 7.92 (s, 1H), 8.03 (d, 1H).

Ethyl 3-(3-aminophenyl)-3-benzenesulphonylamino-propionate (1d)

4.77 g of tin-(II) chloride were added to a solution of 2.0 g of (1c) in 60 ml of ethanol, and the reaction mixture was heated under reflux for 2 h. After cooling, the solution was hydrolysed by pouring it onto ice and adjusted to pH=8 using an NaHCO$_3$ solution (5%). It was then extracted with dichloromethane and the organic phase was washed with NaCl, dried over MgSO$_4$ and concentrated. 1.79 g of a yellow oil were obtained.

$^1$H-NMR (400 MHz, CDCl$_3$): 1.14 (t, 3H), 2.72 (dd, 1H), 2.81 (dd, 1H), 4.02 (q, 2H), 4.65 (q, 1H), 5.66 (d, 1H), 6.41 (m, 1H), 6.48 (m, 2H), 6.96 (t, 1H), 7.40 (m, 2H), 7.50 (m, 1H), 7.75 (m, 2H).

Ethyl 3-benzenesulphonylamino-3-(3-[3-nitrophenylsulphonylamino]-phenyl)-propionate (1e)

382 mg of 3-nitrobenzenesulphonyl chloride were added at 0° C. to a solution of 500 mg of (1d) in 4 ml of pyridine. After a reaction time of 1 h at 0° C. and 2 h at room temperature, the mixture was concentrated, treated with 1 N HCl and extracted with dichloromethane. After drying over MgSO$_4$, the solvent was removed and 649 mg of a solid were obtained.

$^1$H-NMR (400 MHz, CDCl$_3$): 1.02 (t, 3H), 2.50 (dd, 1H), 2.59 (dd, 1H), 3.88 (q, 2H), 4.52 (q, 1H), 5.70 (d, 1H), 6.49 (s, 1H), 6.82–6.90 (m, 3H), 7.06 (t, 1H), 7.34 (t, 2H), 7.44 (t, 1H), 7.59 (t, 1H), 7.64 (d, 2H), 7.96 (d, 1H), 8.31 (d, 1H), 8.49 (m, 1H).

Ethyl 3-(3-[3-aminophenylsulphonylamido]-phenyl)-3-benzenesulphonylamino-propionate (1f)

1.27 g of tin-(II) chloride were added to a solution of 600 mg of (1e) in 9 ml of ethanol, and the reaction mixture was heated under reflux for 2 h. After cooling, the solution was hydrolysed by pouring it onto ice and adjusted to pH=8 using an NaHCO$_3$ solution (5%). It was then extracted with dichloromethane, and the organic phase was washed with NaCl, dried over MgSO$_4$ and concentrated. 394 mg of a yellow, viscous residue were obtained.

¹H-NMR (400 MHz, CDCl₃): 1.14 (t, 3H), 2.65 (dd, 1H), 2.73 (dd, 1H), 4.01 (q, 2H), 4.63 (q, 1H), 5.81 (d, 1H), 6.32 (s, 1H), 6.79 (d, 2H), 6.88 (d, 1H), 6.99 (t, 1H), 7.05–7.14 (m, 3H), 7.22 (t, 1H), 7.39 (m, 2H), 7.51 (t, 1H), 7.71 (d, 2H).

Ethyl 3-benzenesulphonylamino-3-(3-(3-[N,N'-bis-t-butoxycarbonyl-guanidino]-phenylsulphonylamino)-phenyl)-propionate (1g)

0.16 ml of triethylamine, 195 mg of 1,3-bis(t-butoxycarbonyl)-2-methyl-2-thiopseudourea and 132 mg of mercuric chloride were added at 0° C. to a solution of 281 mg of (1f) in 10 ml of DMF. After a reaction time of 30 min at 0° C., the mixture was stirred at room temperature for a further 1.5 h. 15 ml of ethyl acetate were added, and the mixture was stirred for 30 minutes before the precipitate was filtered off. The solution was concentrated and reused without purification.

¹H-NMR (400 MHz, CDCl₃): 1.12 (t, 3H), 1.52 (s, 9H), 1,54 (s, 9H), 2.65 (dd, 1H), 2.72 (dd, 1H), 3.99 (q, 2H), 4.66 (m, 1H), 5.78 (m, 1H), 6.72 (m, 1H), 6.85 (d, 1H), 6.96–7.07 (m, 3H), 7.33–7.49 (m, 5H), 7.65 (d, 2H), 7.78 (m, 1H), 8.12 (s, 1H).

Ethyl 3-benzenesulphonylamino-3-(3-[3-guanidinophenylsulphonylamino]-phenyl)propionate (1h)

2 ml of trifluoroacetic acid were added to a solution of 246 mg of (1g) in 2 ml of methylene chloride. The reaction was stirred at room temperature for 4 h and the solvent was then removed on a rotary evaporator. 100 mg of a viscous oil were obtained by means of chromatographic purification (dichloromethane/methanol 1:1).

Mass spectrometry: 546(MH⁺)

3-Benzenesulphonylamino-3-[3-(3-guanidino-benzenesulphonylamino)-phenyl]-3-propionic acid, trifluoroacetic acid salt (1):

98 mg of lithium hydroxide monohydrate were added to a solution of 98 mg of (1h) in 14 ml of water, and the reaction mixture was stirred at room temperature for 70 h. The solution was acidified to pH=2 using trifluoroacetic acid and concentrated. The crude product was purified by RP chromatography (RP 18 water/acetonitrile). 42 mg of a white solid were obtained.

Elemental analysis for C₂₂H₂₃N₅O₁₁S₂x 2.0 TFA x 2.0H₂O:
calculated: C 39.95;H 3.74; N 8.96 found: C 39.7;H 3.7; N 9.1
Mass spectrometry: 518(MH⁺)

Example 2

General synthesis scheme:

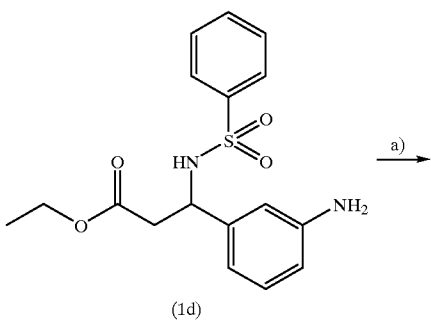

(1d)

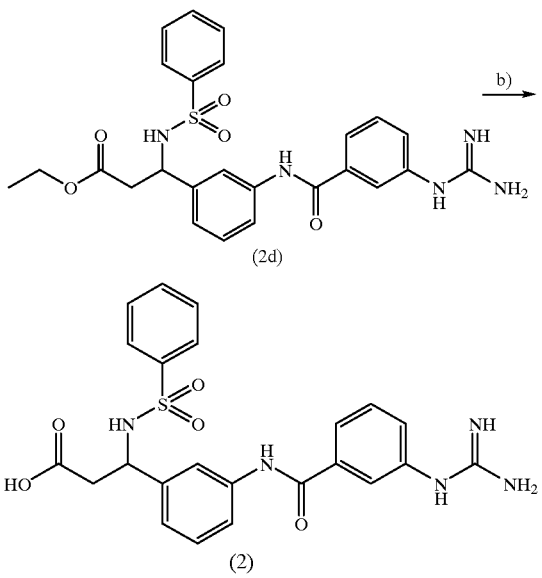

a) 3-H₂N(C=NH)NHC₆H₄COOH (2a), iBuOCOCl, N-methylmorpholine; b) LiOH.

3-((Aminoiminoethyl)amino) benzoic acid hydrochloride (2a)

49.4 g of 3-aminobenzoic acid were added to a solution of 108.7 g of 3,5-dimethylpyrazolyl-1-carboxamidine nitrate and 54.7 g of diisopropylamine in 360 ml of dioxane and 180 ml of water. The reaction solution was heated under reflux for 18 h. After cooling, it was filtered, and the crystallizate was washed with dioxane/water (2:1) and dried in vacuo. The product was dissolved in water and treated with hydrochloric acid, and the hydrochloride salt was obtained after filtration as a solid product (yield: 29.7 g).

Melting point: 261° C.

¹H-NMR (400 MHz, D₄-MeOH): 7.51 (d, 1H), 7.59 (t, 1H), 7.91 (s, 1H), 8.00 (d, 1H).

Ethyl 3-benzenesulphonylamino-3-[3-(3-guanidino-benzoylamino)-phenyl]-propionate (2b)

0.16 ml of N-methylmorpholine and isobutyl chloroformate were added to a solution of 310 mg of (2a) in 5 ml of DMF. The solution was stirred at 0° C. for 5 minutes, then a solution of 500 mg of (1d) in 5 ml of DMF was added at 0° C. The reaction mixture was warmed to RT overnight and then concentrated. A viscous oil (yield: 502 mg) was obtained by chromatographic purification (dichloromethane/methanol=3:1).

Mass spectrometry: 510(MH⁺)

3-Benzenesulphonylamino-3-[3-(3-guanidino-benzoylamino)-phenyl]-propionic acid, trifluoroacetic acid salt (2):

64 mg of lithium hydroxide monohydrate were added to a solution of 204 mg of (2b) in 8 ml of water. The reaction mixture was stirred at room temperature for 48 h. The solution was then acidified to pH=2 using trifluoroacetic acid and concentrated. The crude product was purified by RP chromatography (RP18 water/acetonitrile). A white solid was obtained (yield: 11 mg).

Mass spectrometry: 482(MH⁺)

Example 3

General synthesis scheme:

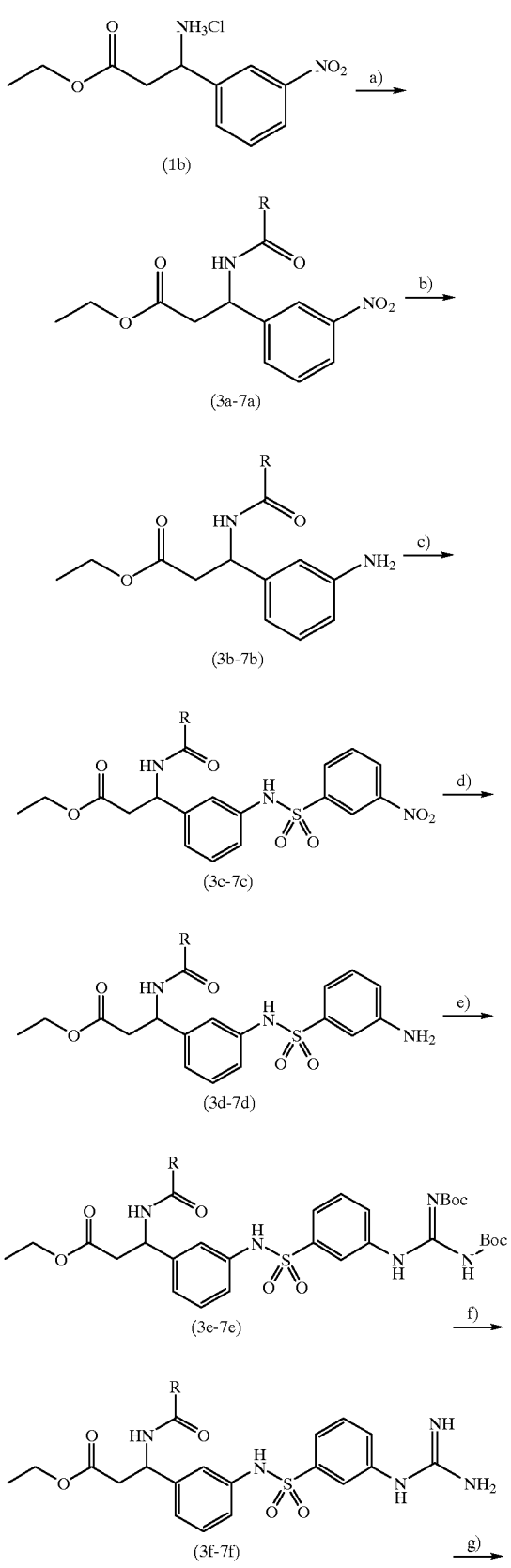

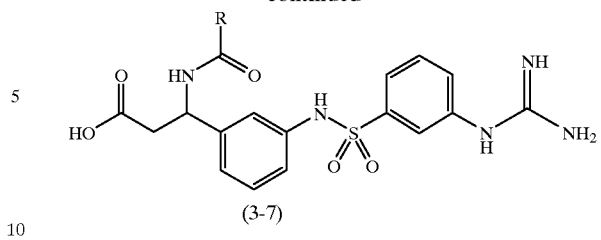

a) RCOCl, iPr$_2$EtN; b) SnCl$_2$, ethanol; c) 3-NO$_2$-C$_6$H$_4$SO$_2$Cl; d) SnCl$_2$, ethanol; e) HgCl$_2$, 1,3-bis(tert-butyloxycarbonyl)-2-methyl-2-thiopseudourea; f) TFA, dichloromethane, g) LiOH.

Ethyl 3-(2,4,6-trimethylphenylacetylamino)-3-(3-nitrophenyl)-propionate (3a):

3.57 g of mesitylacetyl chloride and 5.27 g of diisopropylethylamine were added at 0° C. to a solution of 5.0 g of (1b) in 50 ml of dioxane. The reaction mixture was stirred at 0° C. for 1 h, and was then allowed to warm to room temperature. The solution was added to water and acidified with 1 N HCl, extracted with dichloromethane, dried over MgSO$_4$ and concentrated. Chromatographic purification on silica gel (dichloromethane/methanol 20:1) afforded a white solid (yield: 6.0 g).

$^1$H-NMR (400 MHz, CDCl$_3$): 1.09 (t, 3H), 2.28 (s, 6H), 2.30 (s, 3H), 2.76 (m, 2H), 3.65 (m, 2H), 3.97 (m, 2H), 5.48 (m, 1H), 6.55 (d, 1H), 6.97 (s, 2H), 7.49 (m, 2H), 7.95 (m, 1H), 8.10 (d, 1H).

Ethyl 3-(3-aminophenyl)-3-(2,4,6-trimethylphenylacetylamino)-propionate (3b):

12.5 of tin-(II) chloride were added to a solution of 6.0 g of (3a) in 180 ml of ethanol, and it was heated to reflux for 2 h. The reaction mixture was hydrolysed on ice after cooling and neutralized with NaHCO$_3$ solution (5%), then filtered through a little silica gel and washed with dichloromethane. The organic phase was dried over MgSO$_4$ and concentrated. 1.5 g of a white solid were obtained.

$^1$H-NMR (400 MHz, CDCl$_3$): 1.07 (t, 3H), 2.25 (s, 6H), 2.29 (s, 3H), 2.69 (m, 2H), 3.61 (m, 2H), 3.98 (m, 2H), 5.33 (m, 1H), 6.21 (d, 1H), 6.42 (s, 1H), 6.46 (d, 1H), 6.53 (d, 1H), 6.92 (s, 2H), 7.04 (t, 1H).

Ethyl 3-(3-nitrobenzenesulphonylamino)-phenyl)-3-(2,4,6-trimethylphenylacetylamino)-propionate (3c):

3-Nitrobenzenesulphonyl chloride was added at 0° C. to a solution of 1.5 g of (3b) in 12 ml of pyridine. After a reaction time of 2.5 h, the mixture was concentrated, treated with 1 N HCl and extracted with dichloromethane. After drying over MgSO$_4$, the solvent was removed and 2.02 g of a solid were obtained.

$^1$H-NMR (400 MHz, CDCl$_3$): 1.07 (t, 3H), 2.23 (s, 6H), 2.30 (s, 3H), 2.63 (m, 2H), 3.63 (m, 2H), 3.94 (m, 2H), 5.27 (m, 1H), 6.43 (d, 1H), 6.87–6.95 (m, 5H), 7.14–7.19 (m, 2H), 7.62 (t, 1H), 7.98 (d, 1H), 8.37 (d, 1H), 8.59 (s, 1H).

Ethyl 3-(3-[3-aminobenzenesulphonylamino]-phenyl)-3-(2,4,6-trimethylphenylacetylamino)-propionate (3d):

3.8 g of tin-(II) chloride were added to a solution of 2.0 g of (3c) in 30 ml of ethanol, and the reaction mixture was heated under reflux for 2 h. After cooling the solution, it was hydrolysed by pouring onto ice and neutralized with NaHCO$_3$ solution (5%). The mixture was filtered through a little silica gel, washed with dichloromethane, dried over MgSO$_4$ and concentrated. A yellowish crystalline product was obtained (yield: 1.4 g).

¹H-NMR (400 MHz, CDCl₃): 1.09 (t, 3H), 2.25 (s, 6H), 2.29 (s, 3H), 2.68 (m, 2H), 3.63 (s, 2H), 3.97 (m, 4H), 5.30 (m, 1H), 6.44 (d, 1H), 6.48 (s, 1H), 6.73 (d, 1H), 6.78 (d, 1H), 6.88 (m, 2H), 6.93 (s, 2H), 7.07–7.19 (m, 4H).

Ethyl 3-(2, 4, 6-trimethylphenylacetylamino)-3-(3-[3-N,N'-bis(t-butoxycarbonyl)guanidino-benzenesulphonylamino]-phenyl)-propionate (3e):

0.12 ml of triethylamine, 195 mg of 1,3-bis(t-butoxycarbonyl)-2-methyl-2-thiopseudourea and 132 mg of mercuric chloride were added at 0° C. to a solution of 250 mg of (3d) in 10 ml of DMF. The reaction mixture was stirred at 0° C. for 30 min and at room temperature for 2.5 h. 15 ml of ethyl acetate were added, and it was stirred for 30 min before the precipitate was removed by filtration. The solution was concentrated and reused without purification.

Mass spectrometry: 766(MH⁺)

Ethyl 3-(3-[3-guanidinobenzenesulphonylamino]-phenyl)-3-(2,4,6-trimethylphenylacetylamino)-propionate (3j):

3 ml of trifluoroacetic acid were added to a solution of 266 mg of (3e) in 3 ml of methylene chloride. The reaction mixture was stirred at room temperature for 4 h and concentrated. After chromatographic purification (methylene chloride/methanol=5:1), a viscous oil was obtained (yield: 228 mg).

Mass spectrometry: 566(MH⁺)

3-(3-[3-Guanidinobenzenesulphonylamino]-phenyl)-3-(2,4,6-trimethylphenylacetylamino)-propionic acid, trifluoroacetic acid salt (3):

64 mg of lithium hydroxide monohydrate were added to a solution of 228 mg of (3f) in 30 ml of water and 30 ml of tetrahydrofuran. The reaction mixture was stirred at room temperature for 24 h. The crude product was dried in vacuo and purified by chromatography (acetonitrile/water=7:1). 0.1 ml of trifluoroacetic acid was added and the mixture was concentrated. A white solid was obtained (yield: 100 mg).

Mass spectrometry: 538(MH⁺)

¹H-NMR (400 MHz, D₄-MeOH): 2.18 (s, 6H), 2.23 (s, 3H), 2.73 (m, 2H), 3.60 (m, 2H), 5.18 (m, 1H), 6.84 (s, 2H), 6.97 (d, 1H), 7.04 (d, 1H), 7.10 (s, 1H), 7.20 (t, 1H), 7.39 (d, 1H), 7.51 (m, 2H), 7.68 (d, 1H).

Example 4

Ethyl 3-benzoylamino-3-(3-nitrophenyl)-propionate (4a):

Corresponding to Example 3a, 5.0 g of (1b) were acetylated by addition of benzoyl chloride. A white solid was obtained (yield: 3.3 g).

¹H-NMR (400 MHz, CDCl₃): 1.20 (t, 3H), 3.02 (m, 2H), 4.13 (q, 2H), 5.71 (m, 1H), 7.31–8.68 (m, 10H).

Ethyl 3-(3-aminophenyl)3-benzoylamino-propionate (4b):

Corresponding to Example 3b, 3 g of (4a) were reduced using tin-(II) dichloride. A white solid was obtained (yield: 2.6 g).

¹H-NMR (400 MHz, CDCl₃): 1.19 (t, 3H), 2.91 (dd, 1H), 3.00 (dd, 1H), 4.11 (q, 2H), 5.54 (m, 1H), 6.58 (d, 1H), 6.68 (s, 1H), 6.73 (d, 1H), 7.12 (t, 1H), 7.41–7.52 (m,4H),7.84 (d,2H).

Ethyl 3-benzoylamino-3-(3-(-3-nitrobenzenesulphonylamino)-phenyl)-propionate (4c):

Corresponding to Example 3c, 2.60 g of (4b) were reacted with 3-nitrophenylsulphonyl chloride. A solid was obtained (yield: 1.76 g).

¹H-NMR (400 MHz, CDCl₃): 1.18 (t, 3H), 2.90 (m, 2H), 4.09 (q, 2H), 5.49 (m, 1H), 7.00 (d, 1H), 7.05 (s, 1H), 7.11 (s, 1H), 7.15 (d, 1H), 7.23 (d, 1H), 7.45–7.57 (m, 4H), 7.70 (d, 1H), 7.80 (d, 2H), 7.95 (d, 1H), 8.27 (d, 1H), 8.58 (s, 1H).

Ethyl 3-(3-(3-aminobenzenesulphonylamino)-phenyl)-3-benzoylamino-propionate (4d):

Corresponding to Example 3d, 1.76 g of (4c) were treated with tin-(II) chloride. A yellowish solid was obtained (yield: 779 mg).

¹H-NMR (400 MHz, CDCl₃): 1.20 (t, 3H), 2.93 (m, 2H), 3.98 (s, 2H), 4.12 (q, 2H), 5.52 (m, 1H), 6.48 (s, 1H), 6.67 (d, 1H), 6.84 (d, 1H), 6.90 (s, 1H), 7.08–7.14 (m, 3H), 7.20 (t, 1H), 7.28 (m, 1H), 7.45-7.56 (m, 3H), 7.65 (d, 1H), 7.84 (d, 2H).

Ethyl 3-benzoylamino-3-(3-[3-N,N'-bis(t-butoxycarbonyl)guanidino-benzenesulphonylamino]-phenyl)-propionate (4e):

Corresponding to Example 3e, 1.76 g of (4d) were treated with mercuric chloride and 1,3-bis(tert-butoxycarbonyl)-2-methyl-2-thiopseudourea. 864 mg of the desired product were obtained.

Mass spectrometry: 710(MH⁺)

Ethyl 3-benzoylamino-3-(3-(3-guanidinobenzenesulphonylamino)-phenyl)-propionate (4f):

6 ml of trifluoroacetic acid were added to a solution of 521 mg of (4e) in 6 ml of dichloromethane. The mixture was stirred at room temperature for 4 h, concentrated and purified by chromatography (dichloromethane/methanol=5:1). An oil was obtained (yield: 299 mg).

Mass spectrometry: 510(MH⁺)

3-Benzoylamino-3-[3-(3-guanidino-benzenesulphonylamino)-phenyl]-propionic acid (4):

94 mg of lithium hydroxide monohydrate were added to a solution of 298.5 mg of (4f) in 30 ml of water and 30 ml of THF. The reaction mixture was stirred at room temperature for 20 h and then concentrated. Chromatographic purification on silica gel (acetonitrile/water=7:1) afforded a white solid (yield: 155 mg).

Mass spectrometry: 482(MH⁺)

¹H-NMR (400 MHz, D₄-MeOH): 2.81 (m, 2H), 5.38 (m, 1H), 6.91 (m, 1H), 7.18 (m, 2H), 7.34 (s, 1H), 7.61 (s, 1H), 7.45–7.58 (m, 5H), 7.72 (d, 1H), 7.86 (d, 2H).

Example 5

Ethyl 3-(2,4-dichlorophenylacetylamino)-3-(3-nitrophenyl)-propionate (5a):

Corresponding to Example 3a, 5.0 g of (1b) were acetylated by addition of 2,4-dichlorophenylacetyl chloride. A white solid was obtained (yield: 3.1 g).

¹H-NMR (400 MHz, CDCl₃): 1.15 (t, 3H), 2.87 (m, 2H), 3.73 (s, 2H), 4.05 (q, 2H), 5.47 (m, 1H), 6.99 (d, 1H), 7.18 (d, 1H), 7.29 (m, 1H), 7.47 (s, 1H), 7.50 (d, 1H), 7.59(d, 1H), 8.11 (m,2H).

Ethyl 3-(3-aminophenyl)-3-(2,4-dichlorophenylacetylamino)-propionate (5b):

Corresponding to Example 3b, 3.1 g of (5a) were reduced using tin-(II) dichloride. A white solid was obtained (yield: 0.9 g).

¹H-NMR (400 MHz, CDCl₃): 1.15 (t, 3H), 2.75 (dd, 1H), 2.84 (dd, 1H), 3.64 (s, 2H), 4.03 (q, 2H), 5.31 (m, 1H), 6.55 (m, 4H), 7.08 (t, 1H), 7.27 (m, 2H), 7.43 (s, 1H).

Ethyl 3-(2,4-dichlorophenylacetylamino)-3-(3-[3-nitrophenylsulphonylamino]-phenyl)-propionate (5c):

Corresponding to Example 3c, 900 mg of (5b) were reacted with 3-nitrophenylsulphonyl chloride. A solid was obtained (yield: 1.18 g).

¹H-NMR (400 MHz, CDCl₃): 1.12 (t, 3H), 2.75 (m, 2H), 3.70 (s, 2H), 4.01 (m, 2H), 5.28 (m, 1H), 6.85 (d, 1H), 6.91 (d, 1H), 7.00 (m, 2H), 7.18 (m, 2H), 7.28 (m, 2H), 7.62 (t, 1H), 7.99 (d, 1H), 8.37 (d, 1H), 8.58 (s, 1H).

Ethyl 3-(3-[3-aminophenylsulphonylamino]-phenyl)-3-(2,4-dichlorophenylacetylamino)-propionate (5d):

Corresponding to Example 3d, 1.18 g of (5c) were treated with tin-(II) chloride. 820 mg of a yellowish solid were obtained.

¹H-NMR (400 MHz, CDCl₃): 1.14 (t, 3H), 2.79 (m, 2H), 3.99 (s, 2H), 4.03 (q, 2H), 5.30 (m, 1H), 6.41 (s, 1H), 6.73–6.83 (m, 3H), 6.87 (s, 1H), 6.98 (d, 1H), 7.11–7.33 (m, 6H), 7.43 (d, 1H).

Ethyl 3-(2, 4-dichlorophenylacetylamino)-3-(3-[3-N,N'-bis(t-butoxycarbonyl)guanidino-benzenesulphonylamino]-phenyl)-propionate (5e):

Corresponding to Example 3e, 300 mg of (5d) were treated with mercuric chloride and 1,3-bis(tert-butoxycarbonyl)-2-methyl-2-thiopseudourea. 611 mg of the desired product were obtained.

Mass spectrometry: 792(MH⁺)

Ethyl 3-(2,4-dichlorophenylacetylamino)-3-(3-[3-guanidino-benzenesulphonylamino]-phenyl)-propionate (5j):

Corresponding to Example 4f, 432 mg of (5e) were treated with trifluoroacetic acid. An oil was obtained (292 mg).

Mass spectrometry: 592(MH⁺)

3-(2, 4-Dichlorophenyl)-acetylamino)-3-[3-(3-guanidino-benzenesulphonylamino)phenyl]-propionic acid (5):

Corresponding to Example 4, 292 mg of (5f) were hydrolysed using lithium hydroxide. A white solid was obtained (106 mg).

Mass spectrometry: 564(MH⁺)

¹H-NMR (400 MHz, D₄-MeOH): 2.69 (m, 2H), 3.73 (s, 2H), 5.18 (m, 1H), 6.78 (d, 1H), 7.05 (d, 1H), 7.12 (t, 1H), 7.27 (d, 1H), 7.33 (m, 2H), 7.40 (d, 1H), 7.46 (m, 2H), 7.54 (t, 1H), 7.71 (d, 1H).

Example 6

Ethyl 3-(3-nitrophenyl)-3-phenylpropionylamino-propionate (6a):

Corresponding to Example 3a, 5.0 g of (1b) were acetylated with addition of 3-phenylpropionyl chloride. A white solid was obtained (yield: 6.7 g).

¹H-NMR (400 MHz, CDCl₃): 1.16 (t, 3H), 2.59 (t, 2H), 2.75 (dd, 1H), 2.85 (dd, 1H), 4.05 (q, 2H), 5.45 (m, 2H), 6.75 (d, 1H), 7.20 (m, 3H), 7.25 (m, 2H), 7.45 (d, 2H), 8.06 (s, 1H), 8.10 (m, 1H).

Ethyl 3-(3-aminophenyl)-3-phenylpropionylamino-propionate (6b):

Corresponding to Example 3b, 3.0 g of (6a) were reduced using tin-(II) dichloride. A white solid was obtained (yield: 1.2 g).

¹H-NMR (400 MHz, CDCl₃): 1.17 (t, 3H), 2.51 (t, 2H), 2.68 (dd, 1H), 2.84 (dd, 1H), 2.98 (t, 2H), 3.62 (s, 2H), 4.04 (q, 2H), 5.30 (m, 1H), 6.39 (d, 1H), 6.45 (s, 1H), 6.55 (d, 1H), 7.07 (t, 1H), 7.20 (m, 3H), 7.29 (m, 2H).

Ethyl 3-(3-[3-nitrophenylsulphonylamino]-phenyl)-3-phenylpropionylaminopropionate (6c):

Corresponding to Example 3c, 1.2 g of (6b) were reacted with 3-nitrophenylsulphonyl chloride. A solid was obtained (yield: 1.54 g).

¹H-NMR (400 MHz, CDCl₃): 1.12 (t, 3H), 2.57 (m, 2H), 2.65 (dd, 1H), 2.75 (dd, 1 H), 2.98 (m, 2H), 4.00 (m, 2H), 5.26 (m, 1H), 6.70 (d, 1H), 6.76 (s, 1H), 6.88 (d, 1H), 6.97 (d, 2H), 7.14 (t, 1H), 7.21 (m, 2H), 7.23–7.32 (m, 3H), 7.45 (s, 1H), 7.61 (t, 1H), 8.34 (d, 1H), 8.59 (s, 1H).

Ethyl 3-(3-[3-aminophenylsulphonylamino]-phenyl)-3-phenylpropionylaminopropionate (6d):

Corresponding to Example 3d, 1.53 g of (6c) were treated with tin-(II) chloride. A yellowish solid was obtained (yield: 1.1 g).

¹H-NMR (400 MHz, CDCl₃): 1.16 (t, 3H), 2.57 (t, 2H), 2.68 (dd, 1H), 2.71 (dd, 2H), 2.98 (t, 2H), 4.02 (s, 2H), 4.04 (q, 2H), 5.30 (m, 1H), 6.33 (s 1H), 6.61 (d, 1H), 6.73 (d, 1H), 6.83 (d, 1H), 6.90 (m, 2H), 6.97 (s, 1H), 7.08–7.29 (m, 8H).

Ethyl 3-(3-[3-N,N'-bis(t-butoxycarbonyl)guanidino-benzenesulphonylamino]-phenyl)-3-phenylpropionylamino-propionate (6e):

Corresponding to Example 3e, 500 mg of (6d) were treated with mercuric chloride and 1,3-bis(tert-butoxycarbonyl)-2-methyl-2-thiopseudourea. 1.16 g of the desired product were obtained.

Mass spectrometry: 738(MH⁺)

Ethyl 3-(3-[3-guanidino-benzenesulphonylamino]-phenyl)-3-phenylpropionylaminopropionate (6f):

Corresponding to Example 4f, 1.16 g of (6e) were treated with trifluoroacetic acid. An oil was obtained (yield: 410 mg).

Mass spectrometry: 538(MH⁺)

3-(3-[3-Guanidino-benzenesulphonylamino]-phenyl)-3-phenylpropionylaminopropionic acid (6):

Corresponding to Example 4, 410 mg of (6f) were hydrolysed using lithium hydroxide. A white solid was obtained (yield: 221 mg).

Mass spectrometry: 510(MH⁺)

¹H-NMR (400 MHz, D₄-MeOH): 2.49 (t, 2H), 2.61 (m, 2H), 2.89 (t, 2H), 5.15 (dd, 1H), 6.83 (d, 1H), 6.98 (d, 1H), 7.10 (t, 1H), 7.15–7.24 (m, 5H), 7.28 (s, 1H), 7.37 (s, 1H), 7.47 (d, 1H), 7.55 (t, 1H), 7.72 (d, 1H).

Example 7

Ethyl 3-(3-nitrophenyl)-3-(2-phenylbutyrylamino)-propionate (7a):

Corresponding to Example 3a, 5.0 g of (1b) were acetylated with addition of 2-phenylbutyryl chloride. A white solid was obtained (yield: 6.3 g).

¹H-NMR (400 MHz, CDCl₃): 0.89 (t, 3H), 1.11 (m, 3H), 1.82 (m, 1H), 2.18 (m, 1H), 2.80 (m, 2H), 3.33 (t, 1H), 3.99 and 4.02 (q, 2H), 5.43 (m, 1H), 6.78 (m, 1H), 7.26–8.13 (m, 9H) (mixture of diastereomers).

Ethyl 3-(3-aminophenyl)-3-(2-phenylbutyrylamino)-propionate (7b):

Corresponding to Example 3b, 6.3 g of (7a) were reduced using tin-(II) dichloride. A white solid was obtained (yield: 3.9 g).

¹H-NMR (400 MHz, CDCl₃): 0.88 (m, 3H), 1.09 and 1.15 (t, 3H), 1.80 (m, 1H), 2.19 (m, 1H), 2.61–2.85 (m, 2H), 3.27 (m, 1H), 3.95 and 4.03 (q, 2H), 5.28 (m, 1H), 6.41–6.59 (m, 3H), 6.97 and 7.07 (t, 1H), 7.25–7.37 (m, 5H) (mixture of diastereomers).

Ethyl 3-(3-[3-nitrophenylsulphonylamino]-phenyl)-3-(2-phenylbutyrylamino)propionate (7c):

Corresponding to Example 3c, 3.9 g of (7b) were reacted with 3-nitrophenylsulphonyl chloride. A solid was obtained (yield: 5.0 g).

¹H-NMR (40.0 MHz, CDCl₃): 0.86 and 0.89 (t, 3H), 1.06 and 1.10 (t, 3H), 1.82 (m, 1H), 2.16 (m, 1H), 2.66 and 2.73 (m, 2H), 3.33 and 3.34 (t, 1H), 3.93 (m, 2H), 5.24 (m, 1H), 6.43–8.60 (m, 15H) (mixture of diastereomers).

Ethyl 3-(3-[3-aminophenylsulphonylamino]-phenyl)-3-(2-phenylbutyrylamino)propionate (7d):

Corresponding to Example 3d, 5 g of (7c) were treated with tin-(II) chloride. A yellowish solid was obtained (yield: 1.8 g).

Mass spectrometry: 510(MH⁺)

Ethyl 3-(3-[3-N,N'-bis(t-butoxycarbonyl)guanidino-benzenesulphonylamino]-phenyl)-3-(2-phenylbutyrylamino)-propionate (7e):

Corresponding to Example 3e, 700 mg of (7d) were treated with mercuric chloride and 1,3-bis(tert-butoxycarbonyl)-2-methyl-2-thiopseudourea. 1.45 g of the desired product were obtained.

Mass spectrometry: 752(MH⁺)

Ethyl 3-(3-[3-guanidino-benzenesulphonylamino]-phenyl)-3-(2-phenylbutyrylamino)propionate (7j):

Corresponding to Example 4f, 1.45 g of (7e) were treated with trifluoroacetic acid. An oil was obtained (yield: 630 mg).

Mass spectrometry: 552(MH⁺)

3-(3-[3-Guanidino-benzenesulphonylamino]-phenyl)-3-(2-phenylbutyrylamino)propionic acid (7):

Corresponding to Example 4, 630 mg of (7f) were hydrolysed using lithium hydroxide. A white solid was obtained (yield: 320 mg).

Mass spectrometry: 524(MH⁺)

¹H-NMR (400 MHz, D₄-MeOH): 0.82 and 0.91 (t, 3H), 1.70–2.15 (m, 2H), 2.67 (m, 2H), 3.42 (t, 1H), 5.15 (m, 1H), 6.75–7.73 (m, 13H) (mixture of diastereomers).

Example 8

General synthesis scheme:

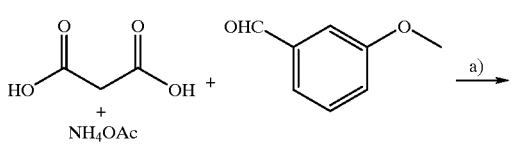

(8a)

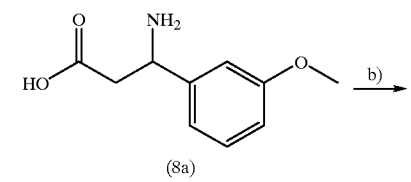

(8b)

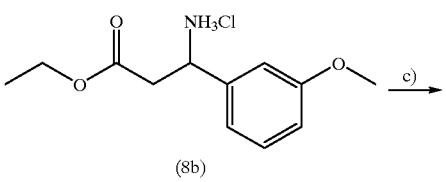

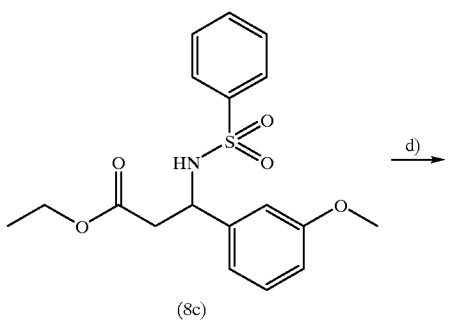

(8c)

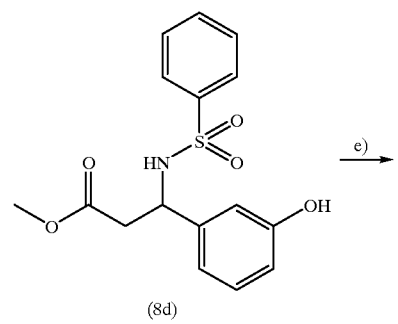

(8d)

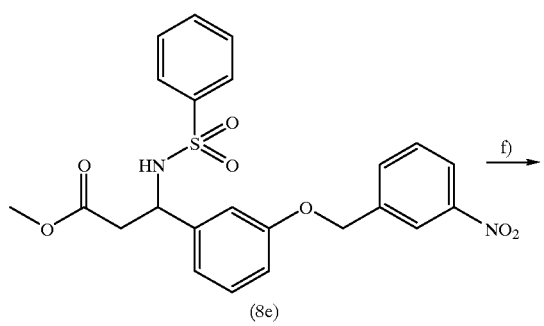

(8e)

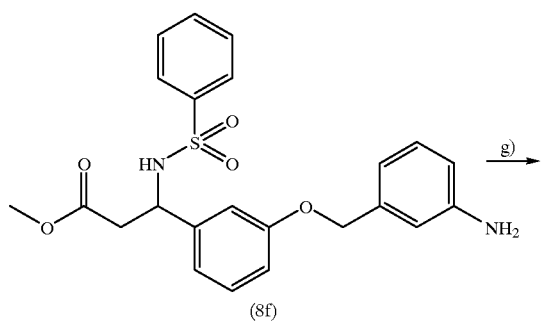

(8f)

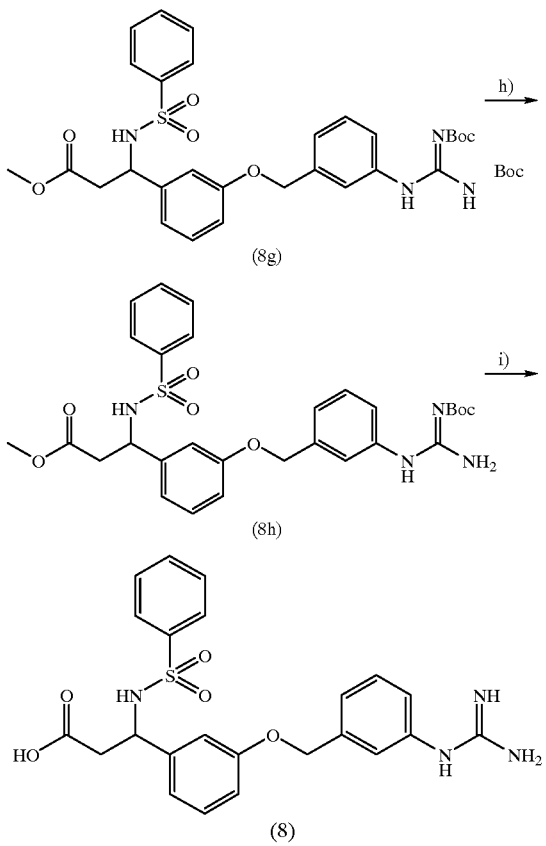

a) 2-propanol, reflux; b) HCl, ethanol; c) PhSO₂Cl, Et₃N; d) BBr₃; e) NaH, 3-NO₂-C₆H₄CH₂Br; f) SnCl₂, ethanol; g) HgCl₂, 1,3-bis(tert-butyloxycarbonyl)-2-methyl-2-thiopseudourea; h) TFA, dichloromethane, i) LiOH.

3-Amino-3-(3-methoxyphenyl)-propionic acid (8a):

Corresponding to Example 1a, 200 g of 3-methoxybenzaldehyde were reacted with ammonium acetate and malonic acid. A white solid was obtained (yield: 135.5 g).

$^1$H-NMR (400 MHz, D$_1$-trifluoroacetic acid): 3.31 (dd, 1H), 3.54 (dd, 1H), 4.03 (s, 3H), 5.00 (m, 1H), 7.19 (m, 3H), 7.52 (t, 1H).

Ethyl 3-Amino-3-(3-methoxyphenyl)-propionate hydrochloride (8b):

Corresponding to Example 1b, 60 g of (8a) were treated with hydrochloric acid in ethanol. A white, crystalline product was obtained (yield: 75 g).

$^1$H-NMR (400 MHz, D$_4$-MeOH): 1.17 (t, 3H), 3.01 (dd, 1H), 3.14 (dd, 1H), 3.82 (s, 3H), 4.14 (m, 2H), 4.70(m, 1H), 6.98 (d, 1H), 7.06 (m, 2H), 7.37 (t, 1H).

Ethyl 3-benzenesulphonylamino-3-(3-methoxyphenyl)-propionate (8c):

Corresponding to Example 1c, 10 g of (8b) were treated with phenylsulphonyl chloride and triethylamine. A yellowish solid was obtained (yield: 13.2 g).

$^1$H-NMR (400 MHz, CDCl$_3$): 1.15 (t, 3H), 2.78 (m, 2H), 3.68 (s, 3H), 4.02 (q, 2H), 4.75 (q, 1H), 5.75 (d, 1H), 6.60 (s, 1H), 6.69 (m, 2H), 7.08 (t, 1H), 7.38 (m, 2H), 7.47 (t, 1H), 7.71 (d, 2H).

Methyl 3-benzenesulphonylamino-3-(3-hydroxyphenyl)-propionate (8d):

A solution of BBr₃ in dichloromethane (1 M) was added at −78° C. to a solution of 2.0 g of (8c) in 50 ml of dichloromethane. After stirring at room temperature for 3 hours, the solution was cooled to −78° C. and 100 ml of methanol were then added. The mixture was stirred at room temperature overnight and then concentrated.

Chromatographic purification (dichloromethane/methanol=40: 1) afforded a white solid (yield: 1.74 g).

$^1$H-NMR (400 MHz, CDCl$_3$): 2.78 (m, 2H), 3.57 (s, 3H), 4.71 (m, 1H), 5.11 (s, 1H), 5.78 (d, 1H), 6.60 (s, 1H), 6.65 (m, 2H), 7.06 (t, 1H), 7.40 (m, 2H), 7.50 (m, 1H), 7.74 (d, 2H).

Methyl 3-benzenesulphonylamino-[3-(3-nitrobenzyloxy)-phenyl]-propionate (8e):

1.5 g of (8d) in 30 ml of THF were added to a suspension of sodium hydride (0.2 g, 60% in paraffin oil) in 10 ml of THF. The reaction mixture was stirred at room temperature for 20 h. After addition of 75 ml of a saturated NH₄Cl solution, the mixture was extracted using ethyl acetate. The combined organic phases were dried over MgSO₄, concentrated and purified by chromatography on silica gel (cyclohexane/ethyl acetate=2 1). 459 mg of the corresponding benzyl ether were obtained.

$^1$H-NMR (400 MHz, CDCl$_3$): 2.79 (in, 2H), 3.57 (s, 3H), 4.75 (m, 1H), 5.03 (s, 2H), 5.78 (d, 1H), 6.78 (m, 3H), 7.16 (t, 1H), 7.41 (m, 2H), 7.51 (m, 1H), 7.58 (t, 1H), 7.75 (m, 3H), 8.21 (d, 1H), 8.29 (s, 1H).

Methyl [3-(3-aminobenzyloxy)-phenyl]-3-benzenesulphonylamino-propionate (8f):

Corresponding to Example 3d, 442 mg of (8e) were treated with tin-(II) chloride. A yellowish solid was obtained (yield: 387 mg).

$^1$H-NMR (400 MHz, CDCl$_3$): 2.79 (m, 2H), 3.56 (s, 3H), 3.72 (br.s, 2H), 4.73 (m, 1H), 4.83 (s, 2H), 5.69 (d, 1H), 6.67 (m, 3H), 6.74 (m, 3H), 7.08 (t, 1H), 7.17 (t, 1H), 7.38 (m, 2H), 7.48 (m, 1H), 7.71 (d, 2H).

Methyl 3-benzenesulphonylamino-3-(3-[3-N,N'-bis(t-butoxycarbonyl)guanidino-benzyl-oxy-phenyl)-propionate (8g):

Corresponding to Example 3e, 382 mg of (8f) were treated with mercuric chloride and 1,³-bis(tert-butoxycarbonyl)-2-methyl-2-thiopseudourea. 563 mg of the desired product were obtained.

Mass spectrometry: 683(MH⁺)

Methyl 3-benzenesulphonylamino-3-(3-[3-guanidino-benzyloxy]-phenyl)-propionate (8h):

Corresponding to Example 4f, 536 mg of (8g) were treated with trifluoroacetic acid. An oil was obtained (yield: 471 mg).

Mass spectrometry: 483(MH⁺)

3-Benzenesulphonylamino-3-[3-(3-guanidino-benzyloxy)-phenyl]-propionic acid (8):

Corresponding to Example 4g, 471 mg of (8h) were hydrolysed using lithium hydroxide. A white solid was obtained (yield: 253 mg).

$^1$H-NMR (400 MHz, D$_4$-MeOH): 2.57 (m, 2H), 4.66 (m, 1H), 5.05 (s, 2H), 6.67 (d, 1H), 6.76 (d, 1H), 6.84 (s, 1H), 7.00 (t, 1H), 7.19 (d, 1H), 7.28 (s, 1H), 7.35–7.49 (m, 5H), 7.67 (d, 2H).

Example 9
General synthesis scheme:

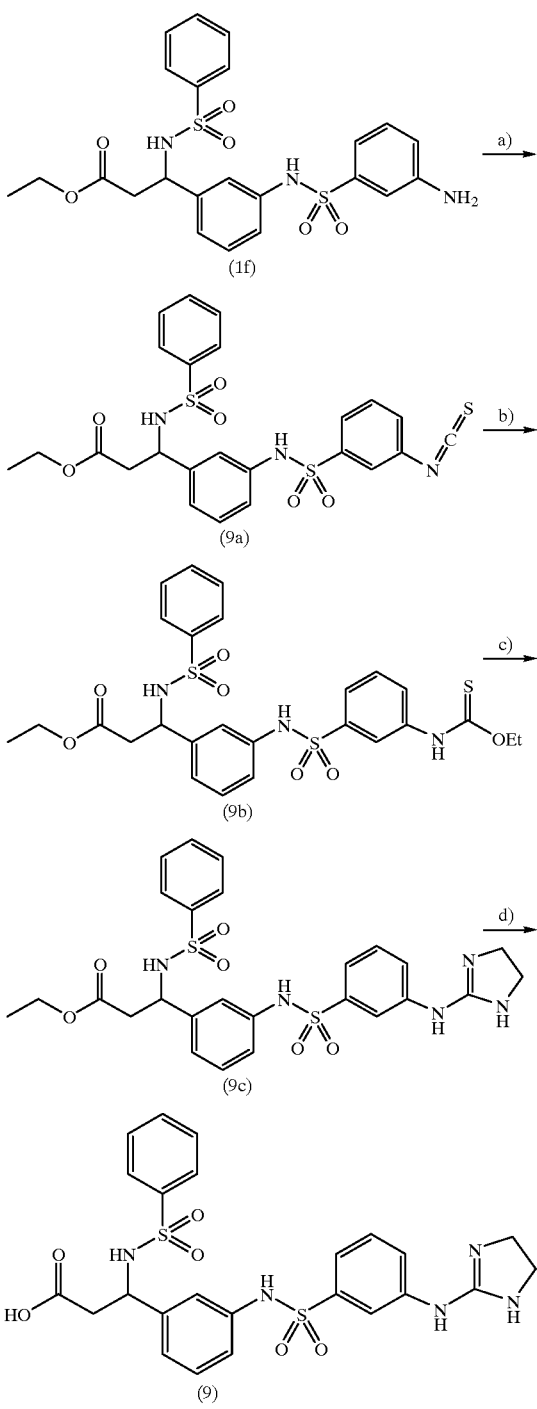

a) thiophosgene; b) ethanol, reflux; c) 1,2-diaminoethane, toluene, reflux; d) LiOH.

Ethyl 3-benzenesulphonylamino-3-(3-[3-isothiocyanatophenylsulphonylamino]-phenyl)-propionate (9a):

A solution of 935 mg of NaHCO$_3$ in 20 ml of water was added to a solution of 800 mg of (1f) in 20 ml of ethyl acetate. The solution was then treated with 207 mg of thiophosgene and stirred for 1 h. After the separation of the two phases, the organic phase was washed with water, dried over MgSO$_4$ and concentrated. After chromatographic purification (dichloromethane/methanol =40:1), the product (9a) was obtained (yield: 636 mg).

$^1$H-NMR (400 MHz, CDCl$_3$): 1.13 (s, 3H), 2.62 (dd, 1H), 2.69 (dd, 1H), 3.99 (q, 2H), 4.66 (m, 1H), 5.91 (d, 1H), 6.74 (s, 1H), 6.90–6.97 (m, 3H), 7.11 (t, 1H), 7.36–7.55 (m, 5H), 7.62 (m, 2H), 7.72 (d, 2H).

Ethyl 3-benzenesulphonylamino-3-(3-[3-ethoxythiocarbonylaminophenylsulphonylamino]-phenyl)-propionate (9b):

200 mg of the compound (9a) were heated overnight in 5 ml of ethanol. The reaction mixture was concentrated. The product was obtained in a yield of 215 mg.

$^1$H-NMR (400 MHz, CDCl$_3$): 1.13 (s, 3H), 1.35 (m, 3H), 2.64 (dd, 1H), 2.75 (dd, 1H), 4.02 (m, 2H), 4.55 (m, 2H), 4.64 (m, 1H), 5.89 (d, 1H), 6.74 (s, 1H), 6.82 (d, 1H), 6.90 (d, 1H), 7.08 (t, 1H), 7.17 (s, 1H), 7.39–7.47 (m, 3H), 7.48–7.65 (m, 3H), 7.73 (d, 2H), 8.80 (s, 1H).

Ethyl 3-benzenesulphonylamino-3-{3-[3-(4, 5-dihydro]H-imidazol-2-yl-amino)-phenylsulphonylamino]-phenyl})-propionate (9c):

215 mg of the compound (9b) and 33 mg of 1,2-diaminoethane were heated overnight in a mixture of 5 ml of toluene and 1 ml of DMF. The reaction mixture was concentrated, and, after chromatographic purification (dichloromethane/methanol=1:1), the compound (9c) was obtained in a yield of 66 mg.

Mass spectrometry: 572 (MH$^+$)

$^1$H-NMR (400 MHz, CDCl$_3$): 1.11 (s, 3H), 2.59 (dd, 1H), 2.66 (dd, 1H), 3.55 (s, 4H), 3.95 (m, 2H), 4.63 (m, 1H), 6.70 (d, 1H), 6.83 (d, 1H), 6.90–6.97 (m, 2H), 7.23 (d, 1H), 7.29 (m, 2H), 7.39–7.49 (m, 4H), 7.54 (d, 2H).

3-Benzenesulphonylamino-3-{3-[3-(4, 5-dihydro-1H-imidazol-2-ylamino)-phenylsulphonylamino]-phenyl}-propionic acid (9):

Corresponding to Example 4g, 66 mg of (9c) were hydrolysed using lithium hydroxide. A white solid was obtained (yield: 47 mg).

Mass spectrometry: 544 (MH$^+$)

$^1$H-NMR (400 MHz, D$_4$-MeOH): 2.52 (dd, 1H), 2.61 (dd, 1H), 3.71 (s, 4H), 4.63 (dd 1H), 6.68 (d, 1H), 6.78–6.96 (m, 2H), 7.17 (s, 1H), 7.37–7.55 (m, 6H), 7.66 (m, 3H).

Biological investigations $\alpha_v\beta_3$ from human A375 cells was purified analogously to a procedure which was described by Wong et al. (Molecular Pharmacology, 50, 529–537 (1996)). 10 µl of $\alpha_v\beta_3$ (5 ng) in TBS pH 7.6, 2 mM CaCl$_2$, 1 mM MgCl$_2$, 1% n-octyl glucopyranoside (Sigma); 10 µl of test substance in TBS pH 7.6, 0.1% DMSO and 45 µl of TBS pH 7.6, 2 mM CaCl$_2$, 1 mM MgCl$_2$, 1 mM MnCl$_2$ were in each case incubated at room temperature for 1 h. 25 µl of WGA SPA beads (Amersham, 4 mg/ml) and 10 µl of echistatin (0.1 µCi, Amersham, chloramine T-labelled) were then added in each case. After 16 hours at room temperature, the samples were measured in a scintillation measuring apparatus (Wallac 1450). The test results are shown in Table 1 below.

TABLE 1

| Example No. | IC$_{50}$-$\alpha_v\beta_3$ (nM) |
| --- | --- |
| 1 | 19 |
| 2 | 390 |

TABLE 1-continued

| Example No. | IC$_{50}$-α$_v$β$_3$ (nM) |
|---|---|
| 3 | 153 |
| 4 | 12.8 |
| 5 | 72.4 |
| 6 | 36.2 |
| 7 | 115 |
| 8 | 33 |
| 9 | 0.295 |

What is claimed is:

1. Compounds of the formula (1)

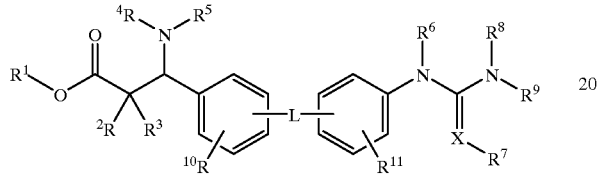

wherein $R^1$ is hydrogen, a substituted or unsubstituted alkyl or cycloalkyl residue, a substituted or unsubstituted aryl residue or a saturated or unsaturated, optionally substituted heterocyclic residue;

$R^2$ is hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, a hydroxyl residue or an alkoxy residue or is bonded to $R^3$ with formation of an optionally substituted carbocyclic or heterocyclic ring system which includes the carbon atom to which $R^2$ is bonded and can optionally contain heteroatoms;

$R^3$ is hydrogen, a substituted or unsubstituted alkyl or cycloalkyl residue, a substituted or unsubstituted aryl residue, a saturated or unsaturated, optionally substituted heterocyclic residue, an optionally substituted alkenyl residue, an optionally substituted alkinyl residue, a hydroxyl residue or an alkoxy residue or is bonded to $R^2$ with formation of an optionally substituted carbocyclic or heterocyclic ring system which includes the carbon atom to which $R^3$ is bonded and can optionally contain heteroatoms;

$R^4$ is —SO$_2$R$^{4'}$, —COOR$^{4''}$, —COR$^{4'}$, —CONR$^{4''}_2$ or —CSNR$^{4''}_2$;

$R^{4'}$ is hydrogen, a substituted or unsubstituted alkyl or cycloalkyl residue, a substituted or unsubstituted aryl residue or a saturated or unsaturated, optionally substituted heterocyclic residue;

$R^{4''}$ is a substituted or unsubstituted alkyl or cycloalkyl residue, a substituted or unsubstituted aryl residue or a saturated or unsaturated, optionally substituted heterocyclic residue;

$R^5$ is hydrogen, a substituted or unsubstituted alkyl or cycloalkyl residue or a substituted or unsubstituted aryl residue;

$R^{10}$ is hydrogen, a substituted or unsubstituted alkyl or cycloalkyl residue, a substituted or unsubstituted alkoxy residue or a halogen atom;

$R^{11}$ is hydrogen, a substituted or unsubstituted alkyl or cycloalkyl residue, a substituted or unsubstituted alkoxy residue or a halogen atom;

L is —(CH$_2$)$_m$NHSO$_2$(CH$_2$)$_n$—, —(CH$_2$)$_m$SO$_2$NH (CH$_2$)$_n$—, —(CH$_2$)$_m$NHCO(CH$_2$)$_n$—, —(CH$_2$)$_m$CONH(CH$_2$)$_n$—, —(CH$_2$)$_m$OCH$_2$(CH$_2$)$_n$—, —(CH$_2$)$_m$CH$_2$O(CH$_2$)$_n$—, —(CH$_2$)$_m$COO(CH$_2$)$_n$—, —(CH$_2$)$_m$OOC(CH$_2$)$_n$—, —(CH$_2$)$_m$CH$_2$CO(CH$_2$)$_n$—, —(CH$_2$)$_m$COCH$_2$(CH$_2$)$_n$—, —NHCONH—, —(CH$_2$)$_m$SCH$_2$(CH$_2$)$_n$—, —(CH$_2$)$_m$CH$_2$S(CH$_2$)$_n$—, —(CH$_2$)$_m$CH$_2$SO(CH$_2$)$_n$—, —(CH$_2$)$_m$SOCH$_2$(CH$_2$)$_n$—, —(CH$_2$)$_m$CH$_2$SO$_2$(CH$_2$)$_n$— or —(CH$_2$)$_m$SO$_2$CH$_2$(CH$_2$)$_n$—, wherein m and n are each an integer of 0 or 1 and m+n≦1;

$R^6$ is hydrogen, a substituted or unsubstituted alkyl or cycloalkyl residue, a substituted or unsubstituted aryl residue, a saturated or unsaturated, optionally substituted heterocyclic residue or is bonded to one of $R^7$, $R^8$ or $R^9$, if present, with formation of an optionally substituted heterocyclic ring system which includes the nitrogen atom to which $R^6$ is bonded and can be saturated or unsaturated and/or can contain further heteroatoms;

x is N, O or S;

$R^7$ is absent, is —H, a substituted or unsubstituted alkyl or cycloalkyl residue, —NO$_2$, —CN, —COR$^{7'}$, —COOR$^{7'}$, or is bonded to one of $R^6$, $R^8$ or $R^9$ with formation of an optionally substituted heterocyclic ring system which includes X and can be saturated or unsaturated and/or can contain further heteroatoms;

$R^{7'}$ is hydrogen, a substituted or unsubstituted alkyl or cycloalkyl residue, a substituted or unsubstituted aryl residue or a saturated or unsaturated, optionally substituted heterocyclic residue which can be saturated or unsaturated and/or can contain further heteroatoms;

$R^8$ is hydrogen, a substituted or unsubstituted alkyl or cycloalkyl residue, a substituted or unsubstituted aryl residue, a saturated or unsaturated, optionally substituted heterocyclic residue or is bonded to one of $R^6$, $R^7$ or $R^9$, if present, with formation of an optionally substituted heterocyclic ring system which includes the nitrogen atom to which $R^8$ is bonded and can be saturated or unsaturated and/or can contain further heteroatoms;

$R^9$ is hydrogen, a substituted or unsubstituted alkyl or cycloalkyl residue, a substituted or unsubstituted aryl residue, a saturated or unsaturated, optionally substituted heterocyclic residue or is bonded to one of $R^6$, $R^7$ or $R^8$, if present, with formation of an optionally substituted heterocyclic ring system which includes the nitrogen atom to which $R^9$ is bonded and can be saturated or unsaturated and/or can contain further heteroatoms;

and their physiologically acceptable salts and stereoisomers.

2. Compounds according to claim 1, characterized in that $R^1$ is hydrogen, a C$_{1-6}$-alkyl residue, a C$_{3-7}$-cycloalkyl residue, an aryl residue or a substituted derivative thereof;

$R^2$ is hydrogen, a C$_{1-6}$-alkyl residue, a C$_{3-7}$-cycloalkyl residue, an aryl residue, an alkenyl residue, an alkinyl residue or a substituted derivative thereof; a hydroxyl residue or a C$_{1-6}$-alkoxy residue or is bonded to $R^3$ with formation of an optionally substituted carbocyclic or heterocyclic ring system which includes the carbon atom to which $R^2$ is bonded and can optionally contain heteroatoms;

$R^3$ is hydrogen, a $C_{1-6}$-alkyl residue, a $C_{3-7}$-cycloalkyl residue, an aryl residue, an alkenyl residue, an alkinyl residue or a substituted derivative thereof; a hydroxyl residue or a $C_{1-6}$-alkoxy residue or is bonded to $R^2$ with formation of an optionally substituted carbocyclic or heterocyclic ring system which includes the carbon atom to which $R^3$ is bonded and can optionally contain heteroatoms;

$R^4$ is $-SO_2R^{4''}$, $-COOR^{4''}$, $-COR^{4'}$, $-CONR^{4''}{}_2$ or $-CSNR^{4''}{}_2$;

$R^{4'}$ is hydrogen, a $C_{1-6}$-alkyl residue, a $C_{3-7}$-cycloalkyl residue, a substituted or unsubstituted aryl residue or a saturated or unsaturated, optionally substituted heterocyclic residue;

$R^{4''}$ is a $C_{1-4}$-alkyl residue, a $C_{3-4}$-cycloalkyl residue, a substituted or unsubstituted aryl residue or a saturated or unsaturated, optionally substituted heterocyclic residue;

$R^5$ is hydrogen, a $C_{1-6}$alkyl residue, a $C_{3-7}$-cycloalkyl residue, an aryl residue or a substituted derivative thereof;

$R^{10}$ is hydrogen, a $C_{1-6}$-alkyl residue, a $C_{3-7}$-cycloalkyl residue, a $C_{1-6}$ alkoxy residue or a substituted derivative thereof or F, Cl, Br or I;

$R^{11}$ is hydrogen, a $C_{1-6}$-alkyl residue, a $C_{3-7}$-cycloalkyl residue, a $C_{1-6}$ alkoxy residue or a substituted derivative thereof or F, Cl, Br or I;

L is $-NHSO_2-$, $-CH_2NHSO_2-$, $-NHSO_2CH_2-$, $-SO_2NH-$, $-CH_2SO_2NH-$, $-SO_2NHCH_2-$, $-NHCO-$, $-CH_2NHCO-$, $-NHCOCH_2-$, $-CONH-$, $-CH_2CONH-$, $-CONHCH_2-$, $-OCH_2-$, $-CH_2OCH_2-$, $-OCH_2CH_2-$, $-CH_2O-$ $-CH_2CH_2O-$, $-COO-$, $-CH_2COO-$, $-COOCH_2-$, $-OOC-$, $-OOCCH_2-$, $-CH_2OOC-$, $-CH_2CO-$, $-COCH_2-$, $-CH_2CH_2CO-$, $-COCH_2CH_2-$, $-CH_2COCH_2-$, $-NHCONH-$, $-SCH_2-$, $-CH_2S-$, $-CH_2SCH_2$, $-SCH_2CH_2-$, $-CH_2CH_2S-$, $-SOCH_2-$, $-CH_2SO-$, $-CH_2SOCH_2-$, $-SOCH_2CH_2-$, $-CH_2CH_2SO-$, $-SO_2CH_2-$, $-CH_2SO_2-$, $-CH_2SO_2CH_2-$, $-CH_2CH_2SO_2-$ or $-SO_2CH_2CH_2-$;

$R^6$ is hydrogen, a $C_{1-6}$-alkyl residue, a $C_{3-7}$-cycloalkyl residue, an aryl residue or a substituted derivative thereof or is bonded to one of $R^7$, $R^8$ or $R^9$, if present, with formation of an optionally substituted heterocyclic ring system which includes the nitrogen atom to which $R^6$ is bonded and can be saturated or unsaturated and/or can contain further heteroatoms;

x is O, N or S;

$R^7$ is absent, is $-H$, a $C_{1-6}$-alkyl residue, a $C_{3-7}$-cycloalkyl residue, $-NO_2$, $-CN$, $-COR^7$, $-COOR^7$, or is bonded to one of $R^6$, $R^7$ or $R^9$ with formation of an optionally substituted heterocyclic ring system which includes X and can be saturated or unsaturated and/or can contain further heteroatoms;

$R^{7'}$ is hydrogen, a $C_{1-6}$-alkyl residue, a $C_{3-7}$-cycloalkyl residue, an aryl residue or a substituted derivative thereof;

$R^8$ is hydrogen, a $C_{1-6}$-alkyl residue, a $C_{3-7}$-cycloalkyl residue, an aryl residue or a substituted derivative thereof or is bonded to one of $R^6$, $R^7$ or $R^9$, if present, with formation of an optionally substituted heterocyclic ring system which includes the nitrogen atom to which $R^8$ is bonded and can be saturated or unsaturated and/or can contain further heteroatoms; and $R^9$ is hydrogen, a $C_{1-6}$-alkyl residue, a $C_{3-7}$-cycloalkyl residue, an aryl residue or a substituted derivative thereof or is bonded to one of $R^6$, $R^7$ or $R^8$, if present, with formation of an optionally substituted heterocyclic ring system which includes the nitrogen atom to which $R^9$ is bonded and can be saturated or unsaturated and/or can contain further heteroatoms.

3. Compounds according to claim 1, characterized in that $R^1$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof;

$R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, $-OH$, methoxy, ethoxy, propoxy, butoxy, pentoxy, hexoxy, benzyloxy or is bonded to $R^3$ with formation of an optionally substituted 3- to 6-membered carbocyclic or heterocyclic ring system which includes the carbon atom to which $R^2$ is bonded and can optionally contain heteroatoms;

$R^3$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, $-OH$, methoxy, ethoxy, propoxy, butoxy, pentoxy, hexoxy, or is bonded to $R^2$ with formation of an optionally substituted 3- to 6-membered carbocyclic or heterocyclic ring system which includes the carbon atom to which $R^3$ is bonded and can optionally contain heteroatoms;

$R^4$ is $-SO_2R^{4'}$ or $-COR^{4'}$;

$R^{4'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, $-C_6H_2(CH_3)_3$, $-C_6(CH_3)_5$, $-CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methylbenzothiazol-2-yl, N-methoxycarbonylpiperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

$R^5$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl or

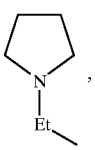 (a1)

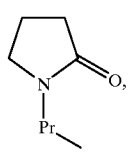 (a2)

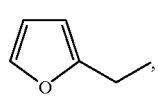 (a3)

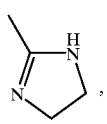 (a4)

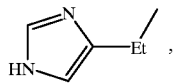 (a5)

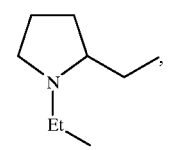 (a6)

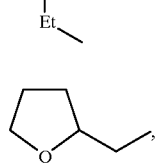 (a7)

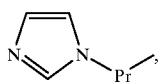 (a8)

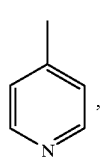 (a9)

-continued

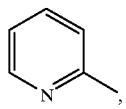 (a10)

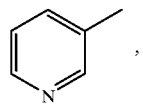 (a11)

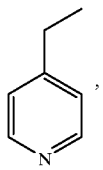 (a12)

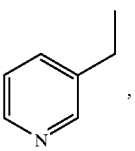 (a13)

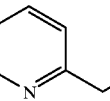 (a14)

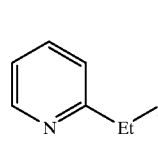 (a15)

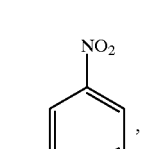 (a16)

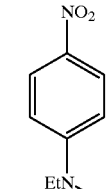 (a17)

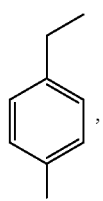 (a18)

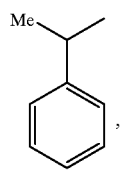

-continued (a19)
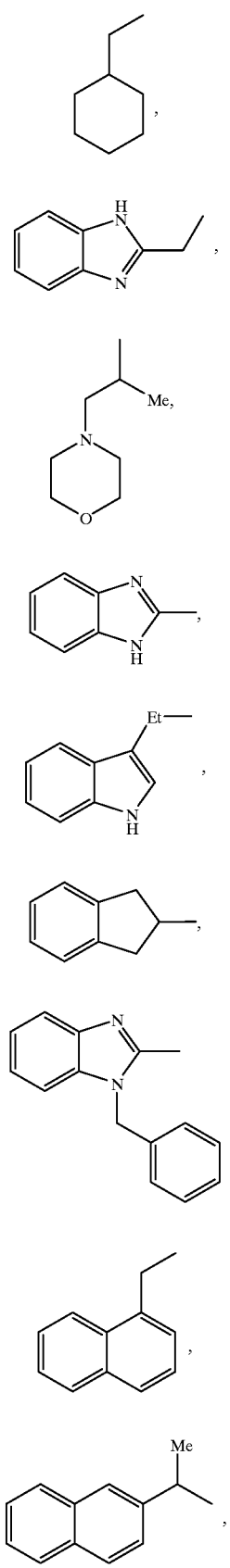

(a20)

(a21)

(a22)

(a23)

(a24)

(a25)

(a26)

(a27)

-continued (a28)
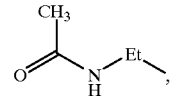

$R^{10}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, methoxy, ethoxy, propoxy, butoxy, pentoxy or hexoxy, fluorine, chlorine, bromine or iodine;

$R^{11}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, methoxy, ethoxy, propoxy, butoxy, pentoxy or hexoxy, fluorine, chlorine, bromine or iodine;

L is —NHSO$_2$—, —CH$_2$NHSO$_2$—, —NHSO$_2$CH$_2$—, —SO$_2$NH—, —CH$_2$SO$_2$NH—, —SO$_2$NHCH$_2$—, —NHCO—, —CH$_2$NHCO—, —NHCOCH$_2$—, —CONH—, —CH$_2$CONH—, —CONHCH$_2$—, —OCH$_2$—, —CH$_2$OCH$_2$, —OCH$_2$CH$_2$—, —CH$_2$— or —CH$_2$CH$_2$O—;

$R^6$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a28) or is bonded to one of $R^7$, $R^8$ or $R^9$, if present, with formation of an optionally substituted heterocyclic 4- to 6-membered ring system which includes the nitrogen atom to which $R^6$ is bonded and can be saturated or unsaturated and/or can contain further heteroatoms;

x is N, O or S;

$R^7$ is absent, is —H, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, —NO$_2$, —CN, —COR$^{7'}$, —COOR$^{7'}$ or is bonded to one of $R^6$, $R^8$ or $R^9$ with formation of an optionally substituted carbocyclic or heterocyclic 4- to 6-membered ring system which includes X and can be saturated or unsaturated and/or can contain further heteroatoms;

$R^{7'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, $R^{8'}$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a28) or is bonded to one of $R^6$, $R^7$ or $R^9$, if present, with forrnation of an optionally substituted heterocyclic 4- to 6-membered ring system which includes the nitrogen atom to which $R^8$ is bonded and can be saturated or unsaturated and/or can contain further heteroatoms; and R⁹ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the residues (a1) to (a28) or is bonded to one of R⁶, R⁷ or R⁸, if present, with formation of an optionally substituted heterocyclic 4- to 6-membered ring system which includes the nitrogen atom to which R⁹ is bonded and can be saturated or unsaturated and/or can contain further heteroatoms.

4. Compounds according to claim 3, characterized in that R⁴ is —SO₂R⁴';

R⁴' is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —NHSO₂—, —CH₂NHSO₂—, —NHSO₂CH₂—;
X is N;
and the other residues are as defined in claim 3.

5. Compounds according to claim 3, characterized in that R⁴ is —COR⁴';

R⁴' is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methylbenzothiazol-2-yl, N-methoxycarbonylpiperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —NHSO₂—, —CH₂NHSO₂— or —NHSO₂CH₂—;
X is N;
and the other residues are as defined in claim 3.

6. Compounds according to claim 3, characterized in that R⁴ is —SO₂R⁴;

R⁴' is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —NHCO—, —CH₂NHCO— or —NHCOCH₂—;

X is N;
and the other residues are as defined in claim 3.

7. Compounds according to claim 3, characterized in that $R^4$ is —$SO_2R^{4'}$;

$R^{4'}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-di-chlorophenyl, 2,6-dichlorophenyl, 4-chlorophenylmethyl, 2,4-dichlorophenylmethyl, 2,6-dichlorophenylmethyl, 2-methoxycarbonyl-phenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —$OCH_2$—, —$CH_2O$—, —$CH_2OCH_2$—, —$CH_2CH_2O$— or —$OCH_2CH_2$—;

X is N;

and the other residues are as defined in claim 3.

8. Compounds according to claim 3, characterized in that $R^4$ is —$SO_2R^{4'}$;

$R^{4'}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

L is —$NHSO_2$—, —$CH_2NHSO_2$— or —$NHSO_2CH_2$—;

X is N;

$R^7$ and $R^9$ together form an ethylene group which bonds the nitrogen atom to which $R^7$ is bonded to the nitrogen atom to which $R^9$ is bonded;

and the other residues are as defined in claim 3.

9. Process for the preparation of compounds of the formula (1) according to claim 1

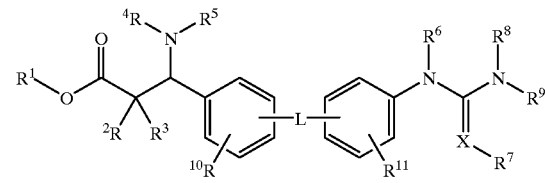
(1)

comprising the steps a) reaction of a β-amino acid of the formula (2)

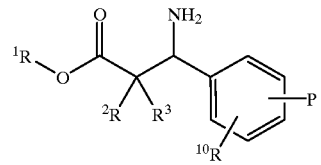
(2)

wherein

P is —$(CH_2)_mNO_2$, —$(CH_2)_mO-C_{1-6}$-alkyl, —$(CH_2)_mSO_2P'$, —$(CH_2)_mCOP'$, —$(CH_2)_mCH_2O-C_{1-6}$-alkyl, wherein m in each case in an integer of 0 or 1;

P' is —OH, —O—$C_{1-6}$-alkyl;

and the other residues are as defined in claim 1 with a compound $R^4$-A to give a compound of the formula (3);

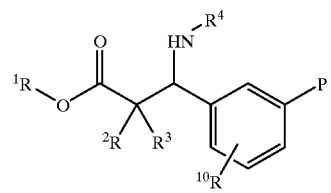
(3)

wherein $R^4$ is —$SO_2R^{4'}$, —$COOR^{4''}$, or —$COR^{4'}$;

$R^{4'}$ and $R^{4''}$ are as defined in claim 1;

A is —Cl, —Br, —I, —O-triflyl, —O-tosyl, —O—C$_{1-6}$- alkyl, —O—CO—C$_{1-4}$-alkyl, —O—CO—O—C$_{1-6}$- alkyl, —OC(CH$_3$)=CH$_2$;
and the other residues are as defined above;

b) conversion of the residue P into the residue Q, wherein
Q is —(CH$_2$)$_m$NH$_2$, —(CH$_2$)$_m$OH, —(CH$_2$)$_m$CH$_2$OH, —(CH$_2$)$_m$SO$_2$A, —(CH$_2$)$_m$COA;
A is as defined above;
m is an integer of 0 or 1;

c) reaction of the compound obtained from step b) with a compound of the formula (4)

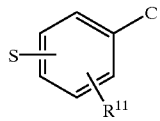

(4)

wherein
S is ASO$_2$(CH$_2$)$_n$—, NH$_2$(CH$_2$)$_n$—, ACO(CH$_2$)$_n$—, HOCH$_2$(CH$_2$)$_n$—, M(CH$_2$)$_n$—, MCH$_2$(CH$_2$)$_n$—, HSCH$_2$(CH$_2$)$_n$— or HS(CH$_2$)$_n$—, wherein n is an integer of 0 or 1;
M is a residue including Mg, Li, Cd or Sn;
A is as defined above; and
C is —NO$_2$ or

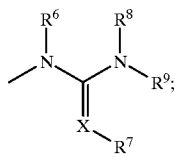

and
X, R$^7$, R$^8$, R$^9$ and R$^{11}$ are as defined in claim 1;
to give a compound of the formula (5)

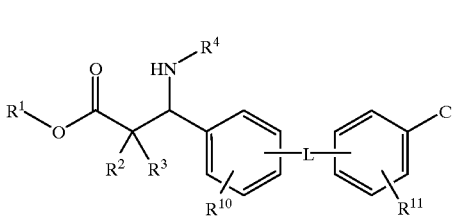

(5)

wherein the residues are as defined in claim 1;

d) if appropriate, conversion of C, if C is a nitro group, into an optionally cyclic urea, thiourea or guanidine unit with obtainment of the compound (1); and e) if appropriate, removal of protective groups and/or derivatization of nitrogen atoms, which are present, at preferred times within the preparation process, and/or conversion of the compound obtained into the free acid and/or conversion of the compound obtained into one of its physiological salts by reaction with an inorganic or organic base or acid.

10. Process according to claim 9, characterized in that the β-amino acid of the formula (2) is obtained by reaction of malonic acid with a benzaldehyde derivative of the formula (2a)

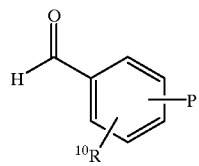

(2a)

wherein R$^{10}$ and P are as defined in claim 9, in the presence of ammonia, ammonium compounds or amines and, if appropriate, subsequent substitution in the α-position to the terminal carboxyl group.

11. Process according to claim 9, characterized in that it comprises the conversion of the nitro group in step d) by reduction to the amino group, subsequent reaction with a carbonic acid derivative and, if appropriate, removal of protective groups present and/or reaction with a compound containing at least one amino group.

12. Pharmaceutical composition, comprising at least one compound according to claim 1 and an excipient or solvent.

13. A method of preventing or treating a disorder selected from cancer, osteolytic diseases, arteriosclerosis, restenosis and opthalmic disorders, said method comprising administering to a patient an effective amount therefor of at least one compound according to claim 1.

14. The method according to claim 13, which is for preventing or treating osteoporosis.

* * * * *